United States Patent
McCullough

(10) Patent No.: US 10,821,240 B2
(45) Date of Patent: *Nov. 3, 2020

(54) METHODS AND DRUG DELIVERY DEVICES USING CANNABIS

(71) Applicant: Vapor Cartridge Technology LLC, Stillwater, MN (US)

(72) Inventor: Timothy McCullough, Stillwater, MN (US)

(73) Assignee: Vapor Cartridge Technology LLC, Stillwater, MN (US)

( * ) Notice: Subject to any disclaimer, the term of this patent is extended or adjusted under 35 U.S.C. 154(b) by 556 days.

This patent is subject to a terminal disclaimer.

(21) Appl. No.: 15/118,090

(22) PCT Filed: Feb. 11, 2015

(86) PCT No.: PCT/US2015/015445
§ 371 (c)(1),
(2) Date: Aug. 10, 2016

(87) PCT Pub. No.: WO2015/123317
PCT Pub. Date: Aug. 20, 2015

(65) Prior Publication Data
US 2016/0354561 A1 Dec. 8, 2016

Related U.S. Application Data

(63) Continuation-in-part of application No. 14/264,999, filed on Apr. 29, 2014, now Pat. No. 9,220,294, and (Continued)

(51) Int. Cl.
*A61M 11/04* (2006.01)
*A24F 47/00* (2020.01)
(Continued)

(52) U.S. Cl.
CPC ......... *A61M 11/042* (2014.02); *A24F 47/008* (2013.01); *A61K 31/05* (2013.01);
(Continued)

(58) Field of Classification Search
CPC .............. A61M 11/041; A61M 11/042; A61M 11/044; A61M 15/00; A61M 15/005; A61M 15/02; A61M 15/06
See application file for complete search history.

(56) References Cited

U.S. PATENT DOCUMENTS 3,270,437 A    9/1966  Castillo et al.
3,625,214 A    12/1971 Higuchi
(Continued)

FOREIGN PATENT DOCUMENTS

WO    WO-1994009842 A1    5/1994
WO    WO-2001076768 A1    10/2001
(Continued)

OTHER PUBLICATIONS

US 9,254,008 B2, 02/2016, McCullough (withdrawn)
(Continued)

*Primary Examiner* — Valerie L Woodward
(74) *Attorney, Agent, or Firm* — Schwegman Lundberg & Woessner, P.A.

(57) ABSTRACT

A method of purifying at least one of THC and CBD from a *cannabis*-containing composition includes heating the *cannabis*-containing composition to a temperature sufficient to volatilize at least one of THC and CBD into a vapor and condensing the vapor on a substrate. A drug delivery cartridge can include a substrate coated with at least one of THC and CBD and configured to allow for passage of air through the cartridge to volatilize at least one of THC and CBD for inhalation by a user to induce a medicinal or therapeutic effect to the user. A drug delivery system can be
(Continued)

used with the drug delivery cartridge and can include a heating element to volatilize at least one of THC and CBD from the coated substrate into a vapor for inhalation.

16 Claims, 23 Drawing Sheets

Related U.S. Application Data a continuation of application No. 14/574,591, filed on Dec. 18, 2014, now Pat. No. 9,380,813, and a continuation-in-part of application No. PCT/US2015/014418, filed on Feb. 4, 2015.

(60) Provisional application No. 61/938,577, filed on Feb. 11, 2014, provisional application No. 62/058,431, filed on Oct. 1, 2014.

(51) Int. Cl.
| | |
|---|---|
| *A61M 15/06* | (2006.01) |
| *H05B 1/02* | (2006.01) |
| *H05B 3/03* | (2006.01) |
| *A61K 31/352* | (2006.01) |
| *A61K 31/05* | (2006.01) |
| *A61M 15/00* | (2006.01) |

(52) U.S. Cl.
CPC ....... *A61K 31/352* (2013.01); *A61M 15/0066* (2014.02); *A61M 15/06* (2013.01); *H05B 1/025* (2013.01); *H05B 3/03* (2013.01); *A61M 15/002* (2014.02); *A61M 15/0028* (2013.01); *A61M 15/0045* (2013.01); *A61M 15/0086* (2013.01); *A61M 2207/00* (2013.01); *H05B 2203/017* (2013.01)

(56) References Cited

U.S. PATENT DOCUMENTS

| | | | |
|---|---|---|---|
| 4,543,275 A | 9/1985 | Akashi et al. | |
| 4,913,865 A | 4/1990 | Toyotama | |
| 4,922,901 A | 5/1990 | Brooks | |
| 5,060,671 A | 10/1991 | Counts et al. | |
| 5,095,921 A | 3/1992 | Losee et al. | |
| 5,224,498 A * | 7/1993 | Deevi | A24F 47/008 128/202.21 |
| 5,269,327 A * | 12/1993 | Counts | A24F 47/008 128/200.14 |
| 5,544,646 A | 8/1996 | Lloyd et al. | |
| 5,878,752 A | 3/1999 | Adams et al. | |
| 5,935,388 A | 8/1999 | Meszaros | |
| 6,045,864 A | 4/2000 | Lyons et al. | |
| 6,095,153 A | 8/2000 | Kessler et al. | |
| 6,270,839 B1 | 8/2001 | Onoe et al. | |
| 6,513,524 B1 | 2/2003 | Storz | |
| 6,589,395 B1 | 7/2003 | Meili | |
| 6,630,507 B1 | 10/2003 | Hampson et al. | |
| 6,909,839 B2 | 6/2005 | Wang et al. | |
| 7,025,992 B2 | 4/2006 | Whittle | |
| 7,088,914 B2 | 8/2006 | Whittle et al. | |
| 7,109,245 B2 | 9/2006 | Kunos et al. | |
| 7,132,128 B2 | 11/2006 | Brcka | |
| 7,215,878 B2 | 5/2007 | Neumann et al. | |
| 7,279,421 B2 | 10/2007 | Suzuki | |
| 7,344,736 B2 | 3/2008 | Whittle et al. | |
| 7,399,872 B2 | 7/2008 | Webster et al. | |
| 7,402,686 B2 | 7/2008 | Duchek | |
| 7,524,881 B2 | 4/2009 | Goodwin et al. | |
| 7,540,286 B2 * | 6/2009 | Cross | A61M 15/0045 128/204.17 |
| 7,622,140 B2 | 11/2009 | Whittle et al. | |
| 7,651,570 B2 | 1/2010 | Brcka | |
| 7,674,922 B2 | 3/2010 | Burdick et al. | |
| 7,700,368 B2 | 4/2010 | Flockhart et al. | |
| 7,709,536 B2 | 5/2010 | WHittle | |
| 7,741,365 B2 | 6/2010 | Makriyannis et al. | |
| 7,763,311 B2 | 7/2010 | Suzuki | |
| 7,816,143 B2 | 10/2010 | Day | |
| 7,913,688 B2 | 3/2011 | Cross et al. | |
| 7,942,147 B2 | 5/2011 | Hodges et al. | |
| 8,034,843 B2 | 10/2011 | Whittle et al. | |
| 8,074,644 B2 | 12/2011 | Hale et al. | |
| 8,147,898 B2 | 4/2012 | Coates | |
| 8,161,979 B1 | 4/2012 | Sinclair, Jr. | |
| 8,387,612 B2 | 3/2013 | Damani et al. | |
| 8,481,091 B2 | 7/2013 | Ross | |
| 8,512,767 B2 | 8/2013 | Ross | |
| 8,910,630 B2 | 12/2014 | Todd | |
| 8,910,640 B2 | 12/2014 | Sears et al. | |
| 9,220,294 B2 | 12/2015 | McCullough | |
| 9,333,229 B2 | 5/2016 | Bjorncrantz | |
| 9,380,813 B2 | 7/2016 | McCullough | |
| 9,408,986 B2 | 8/2016 | McCullough et al. | |
| 9,775,379 B2 | 10/2017 | Davidson et al. | |
| 9,802,011 B2 | 10/2017 | Davidson et al. | |
| 9,839,241 B2 | 12/2017 | Davidson et al. | |
| 9,993,602 B2 | 6/2018 | Davidson et al. | |
| 10,034,990 B2 | 7/2018 | McCullough | |
| D825,102 S | 8/2018 | Bowen et al. | |
| 10,045,567 B2 | 8/2018 | Monsees et al. | |
| 10,045,568 B2 | 8/2018 | Monsees et al. | |
| 10,058,124 B2 | 8/2018 | Monsees et al. | |
| 10,058,129 B2 | 8/2018 | Monsees et al. | |
| 10,058,130 B2 | 8/2018 | Monsees et al. | |
| 10,070,669 B2 | 9/2018 | Monsees et al. | |
| 10,076,139 B2 | 9/2018 | Monsees et al. | |
| 10,080,851 B2 | 9/2018 | Davidson et al. | |
| 10,099,020 B2 | 10/2018 | Davidson et al. | |
| 10,104,915 B2 | 10/2018 | Bowen et al. | |
| 10,111,470 B2 | 10/2018 | Monsees et al. | |
| 10,117,465 B2 | 11/2018 | Monsees et al. | |
| 10,117,466 B2 | 11/2018 | Monsees et al. | |
| 10,118,006 B2 | 11/2018 | Davidson et al. | |
| 10,130,123 B2 | 11/2018 | Hatton et al. | |
| 10,159,282 B2 | 12/2018 | Monsees et al. | |
| 10,166,349 B2 | 1/2019 | Davidson et al. | |
| D842,536 S | 3/2019 | Bowen et al. | |
| 10,231,484 B2 | 3/2019 | Bowen et al. | |
| 10,244,793 B2 | 4/2019 | Monsees et al. | |
| 10,279,934 B2 | 5/2019 | Christensen et al. | |
| D857,879 S | 8/2019 | Kurgan et al. | |
| 10,369,304 B2 | 8/2019 | Davidson et al. | |
| D858,745 S | 9/2019 | Kurgan et al. | |
| D858,868 S | 9/2019 | Bowen et al. | |
| D858,869 S | 9/2019 | Bowen et al. | |
| D858,870 S | 9/2019 | Bowen et al. | |
| D860,523 S | 9/2019 | Cheung et al. | |
| 10,661,036 B2 | 5/2020 | McCullough | |
| 2002/0117175 A1 | 8/2002 | Kottayil et al. | |
| 2003/0131843 A1 | 7/2003 | Lu | |
| 2003/0221625 A1 | 12/2003 | Toda et al. | |
| 2004/0096402 A1 * | 5/2004 | Hodges | A61K 9/007 424/46 |
| 2004/0126326 A1 | 7/2004 | Rabinowitz et al. | |
| 2004/0138293 A1 | 7/2004 | Werner et al. | |
| 2004/0147767 A1 | 7/2004 | Whittle et al. | |
| 2005/0042172 A1 | 2/2005 | Whittle et al. | |
| 2005/0063686 A1 | 3/2005 | Whittle et al. | |
| 2006/0039959 A1 | 2/2006 | Wessling | |
| 2006/0160888 A1 | 7/2006 | Kottayil et al. | |
| 2006/0167084 A1 | 7/2006 | Dudley | |
| 2007/0020193 A1 | 1/2007 | de Vries et al. | |
| 2007/0041994 A1 | 2/2007 | McDowell | |
| 2007/0049645 A1 | 3/2007 | Mechoulam et al. | |
| 2007/0099987 A1 | 5/2007 | Weiss et al. | |
| 2007/0113789 A1 | 5/2007 | Brcka | |
| 2008/0057117 A1 | 3/2008 | Werner et al. | |
| 2008/0112895 A1 | 5/2008 | Kottayil et al. | |
| 2008/0181942 A1 | 7/2008 | Zajicek | |
| 2008/0216828 A1 * | 9/2008 | Wensley | A61K 9/0009 128/203.12 |
| 2008/0255224 A1 | 10/2008 | Blum | |

(56) References Cited

U.S. PATENT DOCUMENTS

| | | |
|---|---|---|
| 2008/0262099 A1 | 10/2008 | Whittle et al. |
| 2008/0275237 A1 | 11/2008 | Arslantas et al. |
| 2008/0306285 A1 | 12/2008 | Hale et al. |
| 2009/0005461 A1 | 1/2009 | Nagarkatti et al. |
| 2009/0197941 A1 | 8/2009 | Guy et al. |
| 2009/0324797 A1 | 12/2009 | Bobzin et al. |
| 2010/0012118 A1 | 1/2010 | Storz |
| 2010/0119606 A1 | 5/2010 | Whittle et al. |
| 2010/0158973 A1 | 6/2010 | Weiss et al. |
| 2010/0204312 A1 | 8/2010 | McAllister et al. |
| 2010/0204443 A1 | 8/2010 | Gazit et al. |
| 2010/0239635 A1 | 9/2010 | McClain et al. |
| 2010/0239693 A1 | 9/2010 | Guy et al. |
| 2010/0249223 A1 | 9/2010 | Di Marzo et al. |
| 2010/0304391 A1 | 12/2010 | Lombard |
| 2011/0036346 A1 | 2/2011 | Cohen et al. |
| 2011/0052694 A1 | 3/2011 | Stinchcomb et al. |
| 2011/0071178 A1 | 3/2011 | Makriyannis et al. |
| 2011/0073120 A1 | 3/2011 | Adamic |
| 2011/0082195 A1 | 4/2011 | Guy et al. |
| 2011/0097283 A1 | 4/2011 | Van Damme et al. |
| 2011/0240022 A1 | 10/2011 | Hodges et al. |
| 2012/0138050 A1* | 6/2012 | Wondka ............... A61M 11/005 128/200.16 |
| 2012/0304990 A1 | 12/2012 | Todd |
| 2012/0311744 A1 | 12/2012 | Sirkowski |
| 2013/0087144 A1 | 4/2013 | Todd |
| 2013/0152922 A1 | 6/2013 | Benassayag et al. |
| 2013/0178453 A1 | 7/2013 | Rohde et al. |
| 2013/0196960 A1 | 8/2013 | Rohde et al. |
| 2013/0255702 A1* | 10/2013 | Griffith, Jr. ........... A24F 47/008 131/328 |
| 2013/0276799 A1 | 10/2013 | Davidson et al. |
| 2013/0284192 A1 | 10/2013 | Peleg et al. |
| 2013/0298905 A1 | 11/2013 | Levin et al. |
| 2014/0041655 A1 | 2/2014 | Barron et al. |
| 2014/0060554 A1* | 3/2014 | Collett ................... H05B 3/265 131/328 |
| 2015/0075546 A1 | 3/2015 | Kueny, Sr. et al. |
| 2015/0136158 A1 | 5/2015 | Stevens et al. |
| 2015/0223515 A1 | 8/2015 | Mccullough |
| 2015/0223523 A1 | 8/2015 | Mccullough |
| 2016/0082203 A1 | 3/2016 | Mccullough et al. |
| 2016/0286860 A1 | 10/2016 | Flayler |
| 2016/0310682 A1 | 10/2016 | Mccullough |
| 2016/0310684 A1 | 10/2016 | Mccullough |
| 2016/0331035 A1 | 11/2016 | Cameron |
| 2016/0331036 A1 | 11/2016 | Cameron |
| 2017/0360089 A1 | 12/2017 | Davidson et al. |
| 2018/0318529 A1 | 11/2018 | Davidson et al. |
| 2018/0344954 A1 | 12/2018 | Davidson et al. |
| 2019/0009039 A1 | 1/2019 | Davidson et al. |
| 2019/0290862 A1 | 9/2019 | Davidson et al. |

FOREIGN PATENT DOCUMENTS

| | | |
|---|---|---|
| WO | WO-2008134668 A2 | 11/2008 |
| WO | WO-2010011464 A1 | 1/2010 |
| WO | WO-2010111232 A9 | 3/2011 |
| WO | WO-2011100359 A1 | 8/2011 |
| WO | WO-2012085919 A2 | 6/2012 |
| WO | WO-2013083631 A1 | 6/2013 |
| WO | WO-2013164761 A1 | 11/2013 |
| WO | WO-2015123064 A1 | 8/2015 |
| WO | WO-2015123317 A1 | 8/2015 |

OTHER PUBLICATIONS

"U.S. Appl. No. 15/201,185, Notice of Allowance dated Mar. 28, 2018", 5 pgs.

"Canadian Application Serial No. 2,939,088, Office Action dated Apr. 16, 2018", 3 pgs.

"Canadian Application Serial No. 2,934,983, Office Action dated Apr. 12, 2018", 3 pgs.

"U.S. Appl. No. 15/201,185, Notice of Allowance dated Jun. 29, 2018", 3 pgs.

"U.S. Appl. No. 15/201,185, Corrected Notice of Allowability dated Jun. 29, 2018", 3 pgs.

"Canadian Application Serial No. 2,934,983, Response filed Oct. 9, 2018 to Office Action dated Apr. 12, 2018", 16 pgs.

"Canadian Application Serial No. 2,939,088, Response filed Oct. 16, 2018 to Office Action dated Apr. 16, 2018", 17 pgs.

"International Application Serial No. PCT/US2015/014418, International Search Report dated Jun. 25, 2015", 4 pgs.

"International Application Serial No. PCT/US2015/014418, Written Opinion dated Jun. 25, 2015", 8 pgs.

"International Application Serial No. PCT/US2015/015445, International Search Report dated May 14, 2015", 4 pgs.

"International Application Serial No. PCT/US2015/015445, Written Opinion dated May 14, 2015", 16 pgs.

Hazekamp, et al., "Evaluation of a Vaporizing Device (Volcano (R)) for the Pulmonary administration of tetrahydrocannabinol", Journal of Pharmaceutical Sciences. vol. 95, (Jun. 2006), 1308-1317.

"Canadian Application Serial No. 2,934,983, Office Action dated Aug. 31, 2017", 3 pgs.

"Canadian Application Serial No. 2,934,983, Response filed Feb. 8, 2018 to Office Action dated Aug. 31, 2017", 35 pgs.

"Canadian Application Serial No. 2,939,088, Response filed Jan. 25, 2018 to Office Action dated Jul. 31, 2017", 126 pgs.

"", Crafty Operating Manual, Storz & Bickel GMBH & Co. KG, (2015), 1-34.

"", Volcano Operating Manual, Storz & Bickel GMBH & Co. KG, (2015), 36 pgs.

"7 Things You Need to Know About Sativex", LeafScience, http://www.leafscience.com/2014/03/08/7-things-need-know-sativex/, (Mar. 8, 2014), 13 pgs.

"710 Pen ARK", About 710pen, [Online]. [Accessed Nov. 28, 2017]. Retrieved from the Internet: <URL: https://www.710penvape.com/pages/about-us-1>, 1 pg.

"Alexza Pharmaceuticals: Staccato Platform Details", [Online]. Retrieved from the Internet: <URL: http://www.alexza.com/staccato/staccato-platform>, (Accessed on: Jun. 30, 2015), 5 pgs.

"Amazon.com: EZ Breathe Atomizer Asthmalnhalers, Model # EZ100: Health & Personal Care", [Online]. Retrieved from the Internet: <URL: http://www.amazon.com/EZ-Breathe-Atomizer-Asthma-Inhalers-EZ-100/dp/B00DQSTVRQ/ref=pd_sxp_f_pt>, (Accessed: Mar. 3, 2015), 25 pgs.

"U.S. Appl. No. 14/264,999, Non Final Office Action dated Mar. 13, 2015", 10 pgs.

"U.S. Appl. No. 14/264,999, Notice of Allowance dated Jul. 2, 2015", 8 pgs.

"U.S. Appl. No. 14/264,999, Notice of Allowance dated Nov. 9, 2015", 8 pgs.

"U.S. Appl. No. 14/264,999, Response filed Jun. 12, 2015 to Non Final Office Action dated Mar. 13, 2015", 16 pgs.

"U.S. Appl. No. 14/574,591, Non Final Office Action dated Aug. 18, 2015", 14 pgs.

"U.S. Appl. No. 14/574,591, Notice of Allowance dated Feb. 12, 2016", 5 pgs.

"U.S. Appl. No. 14/574,591, Notice of Allowance dated May 20, 2016", 5 pgs.

"U.S. Appl. No. 14/574,591, Notice of Allowance dated Nov. 24, 2015", 5 pgs.

"U.S. Appl. No. 14/574,591, Response filed Jun. 30, 2015 to Restriction Requirement dated May 21, 2015", 9 pgs.

"U.S. Appl. No. 14/574,591, Restriction Requirement dated May 21, 2015", 5 pgs.

"U.S. Appl. No. 14/574,591, Response filed Oct. 30, 2015 to Non Final Office Action dated Aug. 18, 2015", 44 pgs.

"U.S. Appl. No. 14/959,591, Non Final Office Action dated Feb. 1, 2016", 12 pgs.

"U.S. Appl. No. 14/959,591, Notice of Allowance dated Jun. 8, 2016", 8 pgs.

"U.S. Appl. No. 14/959,591, Preliminary Amendment filed Dec. 10, 2015", 6 pgs.

(56) References Cited

OTHER PUBLICATIONS

"U.S. Appl. No. 14/959,591, Response filed Apr. 29, 2016 to Non Final Office Action dated Feb. 1, 2016", 24 pgs.
"U.S. Appl. No. 15/199,366 Response filed Nov. 22, 2017 to Non Final Office Action dated Aug. 25, 2017.", 10 pgs.
"U.S. Appl. No. 15/199,366, Non Final Office Action dated Aug. 25, 2017", 13 pgs.
"U.S. Appl. No. 15/201,185, Non Final Office Action dated Aug. 25, 2017", 8 pgs.
"U.S. Appl. No. 15/201,185, Response filed Nov. 27, 2017 to Non Final Office Action dated Aug. 25, 2017", 7 pgs.
"Big Pharma's Weed Winner", [online]. The Daily Beast. [retireved on Apr. 29, 2014]., Retrieved from the Internet: <URL: http://www.thedailybeast.com/articles/2014/01/24/how-one-pharmaceutical-company-could-become-the-safest-and-most-trusted-of-all-cannabis-dealers.html#url=/articles/2014/01/24/how-one-pharmaceutical-company-could-become-, (Jan. 24, 2014), 19 pgs.
"Canadian Application Serial No. 2,939,088, Office Action dated Jul. 31, 2017", 3 pgs.
"Clean Your Volcano! How Often?" Volcano Vaporizer Tips n' Tricks, [Online]. Retrieved from the Internet: <URL: http://volcanotips.com/volcano/clean-your-volcano-how-often/, (Accessed Feb. 19, 2016), 4 pgs.
"Compare vaporizers", STORZ & BICKEL, [Online]. [Accessed Nov. 28, 2017]. Retrieved from the Internet: <URL: https://www.storz-bickel.com/us/en/compare/, 4 pgs.
"CRAFTY", SKU 01 00 CY- STORZ & BICKEL, [Online]. [Accesed Nov. 28, 2017]. Retrieved from the Internet: <URL: https://www.storz-bickel.com/us/en/crafty.html>, 5 pgs.
"Crafty Vaporizer", STORZ & BICKEL, [Online]. [Accessed Nov. 28, 2017]. Retrieved from the Internet: <URL: https://www.storz-bickel.com/us/en/crafty/>, 4 pgs.
"Decarboxylating Cannabis: Turning THCA into THC", [online}. [Retrieved on Apr. 29, 2014]. Retrievefd from the Internet: <URL: http://www.marijuanagrowershq.com/decarboxylating-cannabis-turning-thca-into-thc/>, (Aug. 14, 2012), 36 pgs.
"Decarboxylation of cannabis: scientific info about temps and times", [online]. [Archived on Jul. 5, 2013]. Retrieved from the Internet: <URL: http://cannabischris.com/2012/10/decarboxylation-of-cannabis/>, (Oct. 31, 2012), 5 pgs.
"Dr. Sisley Recieves Government Grant to Research Cannabis and PTSD", [Online]. Retrieved from the Internet: <URL: https://www.cannabisreports.com/news/2014/12/17/dr-sisley-receives-government-grant-to-research-cannabis-and-ptsd/>, (Dec. 17, 2014), 10 pgs.
"Edibles in Review: LickIt Cannabis-Infused Breath Strips—Drugs Forum", [Online]. Retrieved from the Internet: <URL: https://drugs-forum.com/forum/showthread.php?t=220406>, (Accessed Apr. 26, 2016), 3 pgs.
"Evaluation of Volcano(r) Vaporizer for the Efficient Emission of THC, CBD, CBN and the Significant Reduction and/or Elimination of Polynuclear-Aromatic (PNA) Analytes Resultant of Pyrolysis", prepared by Chemic Laboratories, Canton, MA [online}. [Retrieved on Apr. 29, 2016]. Retrieved from the Internet: <URL: http://www.maps.org/mmj/vaporizerstudy4.15.03.pdf>, (2003), 57 pgs.
"Hash Oil", [online]. [Retrieved on Apr. 29, 2014]. Retrieved from the Internet: <URL: http://en.wikipedia.org/wiki/Hash_oil>, (last modified on Apr. 27, 2014), 4 pgs.
"Haze Vaporizer", Guest Post—Best Marijuana Vaporizers for Your Health, [Online]. [Accessed Nov. 28, 2017]. Retrieved from the Internet: <URL: https://www.marijuana.com/news/2014/12/best-marijuana-vaporizers-for-your-health/>, (Dec. 11, 2014), 11 pgs.
"Heliospectra AB hires Dr. Sue Sisley as Director of Medicinal Plant Research", Heliospectra, [Online]. Retrieved from the Internet: <URL: https://www.heliospectra.com/blog/heliospectra-ab-hires-dr-sue-sisley-director-medicinal-plant-research>, (Feb. 23, 2015), 6 pgs.
"Herbal Vaporizer, Ingesting herbs has some incredible health benefits", Natural Health Ezine, [Online]. Retrieved from the Internet: <URL: http://naturalhealthezine.com/herbal-vaporizers-an-introduction/>, (Jan. 9, 2011), 5 pgs.

"History: GW Pharmaceuticals", [Online]. Retrieved from the Internet: <URL: http://www.gwpharm.com/history.aspx>, (Accessed on: Jun. 30, 2015), 5 pgs.
"How to Use Your Inhaler", Asthma Society of Canada, [Online]. Retrieved from the Internet: <URL: http://www.asthma.ca/adults/treatment/spacers.php, (Oct. 2015), 3 pgs.
"International Application Serial No. PCT/US2015/014418, International Preliminary Report on Patentability dated Aug. 25, 2016", 10 pgs.
"International Application Serial No. PCT/US2015/014418, Invitation to Pay Additional Fees and Partial Search Report dated Apr. 20, 2015", 2 pgs.
"International Application Serial No. PCT/US2015/015445, International Preliminary Report on Patentability dated Aug. 25, 2016", 18 pgs.
"JUJU Joints: Home page", [Online]. Retrieved from the Internet: <URL: http://jujujoints.com/>, (Accessed on: Jun. 30, 2015), 1 pg.
"JUJU Joints: The Deets", [Online]. Retrieved from the Internet: <URL: http://jujujoints.com/deets/>, (Accessed on: Jun. 30, 2015), 3 pgs.
"Open Vape—Products: O.PENVAPE Battery & Charger", [Online]. Retrieved from the Internet: <URL: http://www.openvape.com/shop/shop/featured-products/o-penvape-battery.html?SID=h9susctdi7uc88huscks6je2o0>, (Accessed on: Jun. 30, 2015), 3 pgs.
"Open vape: Home page", [Online]. Retrieved from the Internet: <URL: http://www.openvape.com/>, (Accessed on: Jun. 30, 2015), 2 pgs.
"Sativex(r)", [online]. (c) 2014 GW Pharmaceuticals. [Retrieved on Apr. 29, 2014]. Retrieved from the Internet: <URL: http://www.gwpharm.com/Sativex.aspx>, (2014), 2 pgs.
"Science Minus Details: Weed Science or Activation Explained!!", [Online]. Retrieved from the Internet: <URL: http://www.scienceminusdetails.com/2009/04/weed-science.html, (2009), 17 pgs.
"The ARK by 710 Pen—Three pens, nine cartridges, ONE ARK!" Copyright 710 Pen, 2011-2014, [Online]. [Accessed Nov. 28, 2017]. Retrieved from the Internet: <URL: https://wvvw.710penvape.com/products/the-new-710-ark-everything-you-need-in-1-kit>, 2 pgs.
"Total Sublimation—Sublimator in Action", [online]. [Retrieved on Apr. 29, 2014]. Retrieved from the Internet: <URL: http://thehighcanadian.wordpress.com/tag/total-sublimation/>, (2014), 3 pgs.
"Tutorial: Atomizer vs. Cartomizer vs. Clearomizer Overview of Atomizer vs. Cartomizer vs. Clearomizer", [Online]. Retrieved from the Internet: <URL: https://www.misthub.com/blog/tutorialatomizervscartomizenisclearomizer/>, (Accessed: Mar. 3, 2015), 15 pgs.
"Vacuum and fractional distillation", [online]. [Retrieved on Apr. 29, 2014]. Retrieved from the Internet: <URL: http://boards.cannabis.com/concentrates/182951-vacuum-fractional-distillation.html>, (2014), 5 pgs.
"Vaporizer (inhalation device)", [online]. Wikipedia(r), the free encyclopedia. [Retrieved on Apr. 29, 2014]. Retrieved from the Internet: <URL: http://en.wikipedia.org/wiki/vaporizer(inhalation_device)>, (modified on Mar. 21, 2014), 4 pgs.
"Volcano Vaporizer", [online]. Copyright 2013 Storz and Bickel GMBH and Co. KG. [Retrieved on Dec. 10, 2013]. Retrieved from the Internet: <URL: http://volcanovaporizer.com/about/>, (2013), 4 pgs.
"Volcano(r) Vaporization System", [online]. [Retrieved on May 15, 2014]. Retrieved from the Internet: <URL: http://www.storz-bickel.com/vaporizer/volcano-technology.html>, (2014), 4 pgs.
"Why Vaporize?" Copyright 2013 Storz and Bickel GMBH and Co. KG. [Retrieved on Dec. 10, 2013]. Retrieved from the Internet: <URL: http://volcanovaporizer.com/whv-vape/>, (2013), 4 pgs.
Chambers, Rachel, "Leafly: What is Dabbing and How Do Dabs Work?" [Online]. Retrieved from the Internet: <URL: https://www.leafly.com/news/cannabis-101/is-dabbing-good-or-bad-or-both>, (Oct. 28, 2013), 9 pgs.
Cross, Green, "THC is heat activated: Rollitup", [Online]. Retrieved from the Internet: <URL: http://www.rollitup.org/t/thc-is-heat-activated.242205/>, (Accessed Apr. 26, 2016), 7 pgs.
Doblin, Rick, "HHS Cover Letter", Multidisciplinary Association for Psychedelic Studies (MAPS), [Online]. Retrieved from the

(56) References Cited

OTHER PUBLICATIONS

Internet: <URL: http://www.maps.org/research-archive/mmj/HHS-CoverLetter-Doblin-electronic-14Mar14.pdf>, (Mar. 12, 2014), 2 pgs.

Fraleigh, Nicholas, "Backdoor Medicine: How Cannabis Suppositories Can Save Lives—Cannabis Digest", [Online]. Retrieved from the Internet: <URL: http://cannabisdigest.ca/cannatory/>, (2014), 53 pgs.

Hazekamp, Arno, "", Cannabis Extracting the Medicine Hazekamp Thesis, (2007), 187 pgs.

Jimbob, "THC coated rolling papers: Cannabis.com—The World's Cannabis Site", [Online]. Retrieved from the Internet: <URL: http://boards.cannabis.com/threads/thc-coated-rolling-papers.114509/>, (Accessed Apr. 26, 2016), 7 pgs.

Mechoulam, Raphael, "Veterans for medical cannabis access: General use of cannabis for PTSD Symptoms", [Online]. Retrieved from the Internet: <URL: http://veteransformedicalmarijuana.org/content/general-use-cannabis-ptsd-symptoms>, (2010), 3 pgs.

Schwartz, Carly, "Marijuana Market Poised to Grow Faster Than Smartphones", [online]. Huffington Post. [Retrieved on Apr. 29, 2014]. Retrieved from the Internet: <URL: http://www.huffingtonpost.com/2013/11/04/marijuana-market_n_4209874.html>, (2013), 6 pgs.

Wattenberg, Sarah, "Letter to Multidisciplinary Association for Psychedelic Studies (MAPS)", [Online]. Retrieved from the Internet: <URL: http://www.maps.org/research-archive/mmj/CoverletterSarahW_10-23_2013_final_forweb.pdf, (Oct. 23, 2013), 14 pgs.

Welch, William M., "Vaporizers, e-cigs of the pot world, are booming", [online]. USA Today. [Retrieved on Apr. 29, 2014]. Retrieved from the Internet: <URL: http://www.usatoday.com/story/money/business/2014/03/15/marijuana-vapporizing-gains/6042675/>, (Mar. 17, 2014), 6 pgs.

Whittle, G. W, et al., "Prospect for new cannabis-based prescription medicines", Journal of Cannabis Therapeutics 3(4), (2001), 133-152.

"Canadian Application Serial No. 2,939,088, Office Action dated Jan. 8, 2019", 3 pgs.

"U.S. Appl. No. 15/199,366, Final Office Action dated Nov. 21, 2019", 11 pgs.

"U.S. Appl. No. 15/199,366, Notice of Allowance dated Feb. 5, 2020", 5 pgs.

"U.S. Appl. No. 15/199,366, Response filed Jan. 21, 2020 to Final Office Action dated Nov. 21, 2019", 7 pgs.

"U.S. Appl. No. 15/199,366, Corrected Notice of Allowability dated Mar. 18, 2020", 2 pgs.

"Canadian Application Serial No. 2,939,088, Response filed Jul. 5, 2019 to Office Action dated Jan. 8, 2019", 11 pgs.

"The World's First Programmable Drug Delivery System", Syqe Medical, [Online] Retrieved from the Internet: <URL: https://www.syqemedical.com/>, (Retrieved on Feb. 6, 2020), 16 pgs.

Greenberg, Tzally, "Eight Years and 83 Million Later, Syqe Medical Releases First Cannabis Inhaler", CTECH by Calcalist, [Online] Retrieved from the Internet: <URL: https://www.calcalistech.com/ctech/articles/0,7340,L-3764680,00.html>, (Jun. 20, 2019), 5 pgs.

June-Wells, Mark, "Your Guide to Supercritical Extraction", Cannabis Business Times, [Online] Retrieved from the Internet on Oct. 1, 2019: <URL: https://www.cannabisbusinesstimes.com/article/your-guide-to-supercritical-extraction/>, (Mar. 2018), 7 pgs.

\* cited by examiner

METHODS AND DRUG DELIVERY DEVICES USING CANNABIS

CLAIM OF PRIORITY

This application is a U.S. National Stage Filing under 35 U.S.C. 371 from International Application No. PCT/US2015/015445, filed on Feb. 11, 2015, which claims the benefit of priority to U.S. Provisional Application No. 61/938,577, entitled "METHODS AND DEVICES USING *CANNABIS* VAPORS", filed on Feb. 11, 2014; the benefit of priority to U.S. Provisional Application No. 62/058,431, entitled "DRUG DELIVERY SYSTEM AND METHOD", filed on Oct. 1, 2014; the benefit of priority to U.S. patent application Ser. No. 14/264,999, entitled "METHODS AND DEVICES USING *CANNABIS* VAPORS", filed on Apr. 29, 2014; the benefit of priority to U.S. patent application Ser. No. 14/574,591, entitled "DRUG DELIVERY SYSTEM AND METHOD", filed on Dec. 18, 2014; and the benefit of priority to International Application Serial No. PCT/US2015/014418, entitled "METHODS AND DRUG DELIVERY DEVICES USING *CANNABIS*", filed on Feb. 4, 2015, each of which is hereby incorporated by reference herein in its entirety. International Application No. PCT/US2015/015445 is a continuation-in-part of U.S. patent application Ser. No. 14/264,999, a continuation-in-part of U.S. patent application Ser. No. 14/574,591, and a continuation in part of International Application Serial No. PCT/US2015/014418.

TECHNICAL FIELD

The present application relates to methods and devices using *cannabis*, and more particularly, to methods of purifying at least one of THC and CBD from *cannabis* to create drug delivery products containing THC or CBD.

BACKGROUND

*Cannabis*, otherwise known as marijuana, is a naturally occurring plant with at least two well-known pharmacologically active components, tetrahydrocannabinol (THC) and cannabidiol (CBD). When ingested, THC and CBD can provide numerous benefits and can be used, for example, to alleviate pain, muscle spasticity and in the treatment of nausea associated with chemotherapy.

Smoking of the *cannabis* material is a common form of THC and CBD ingestion. However, while THC and CBD are released by smoking, combustion of the *cannabis* material can also release many toxic substances such as ammonia and hydrogen cyanide that can cause damage if ingested. Ingestion of foods laced with *cannabis* material can deliver THC and CBD to the body. However, any other undesirable materials in the *cannabis* are also ingested and the dosage of THC and CBD can be inconsistent and hard to determine.

Isolation and purification of THC and CBD from *cannabis* can be of great interest and benefit to the medical community. A way to purify THC and CBD from *cannabis* and convert the purified THC and CBD into an easily-ingestible form is desired.

GOALS OF THE INVENTION

There is an opportunity for a drug delivery product that allows for inhalation of at least one of THC and CBD without inhaling other undesirable components found in raw *cannabis* or created by burning the raw *cannabis*. The amount and purity of THC or CBD in the drug delivery product can be controlled for dosage. The drug delivery product can be formed using a separation and coating process, as described herein, that facilitates controlled deposition of THC or CBD onto a substrate to form the drug delivery product.

SUMMARY OF THE INVENTION

The at least one present invention is directed to methods for purifying tetrahydrocannabinol (THC) and cannabidiol (CBD) from *cannabis* plant material; providing substrates containing or incorporating the purified THC and CBD; and providing apparatuses for delivery of at least one of THC and CBD to patients and consumers.

In a first aspect of the invention, the method is directed to controlled volatilization of at least one of THC and CBD from preferably comminuted *cannabis* plant material and absorption, deposition, adsorption or otherwise condensing the volatilized THC or CBD or both on a substrate held at a temperature to assure capture of the volatilized THC, CBD or both.

A second aspect of the invention is directed to the substrate with deposited THC, CBD or both. The substrate with THC, CBD or both is constructed and configured to enable release of the THC, CBD or both upon controlled heating. This aspect can include controlled release of the THC, CBD or both so as to provide regulated, controlled, limited doses of THC, CBD or both over time. In a third aspect of the invention, the substrate with deposited THC, CBD or both is converted into a drug delivery cartridge. The drug delivery cartridge can be used with a controllable heating element to volatilize and inhale the THC, CBD or both.

A third aspect of the invention is directed to a drug delivery system which can include a drug delivery cartridge formed from a substrate described above. In an example, the drug delivery cartridge can include a cylindrical structure extending in a longitudinal direction and formed from an electrically conductive material. The cylindrical structure can include multiple electrodes extending laterally across the substrate at respective longitudinal locations. Each of the electrodes has an electrical resistance small enough to conduct current laterally along the substrate without heating the cylindrical structure. The cylindrical structure can include at least one substrate portion extending longitudinally between a respective pair of electrodes. Each substrate portion can have an electrical resistance high enough to conduct current longitudinally between the electrodes and resistively heat the respective substrate portion in response to the current conducted therethrough. A dose of a drug can be disposed on each substrate portion and configured to volatilize into a gas in response to the resistive heating of the respective substrate portion.

This Summary is intended to provide an overview of subject matter of the present patent application. It is not intended to provide an exclusive or exhaustive explanation of the invention. The Detailed Description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
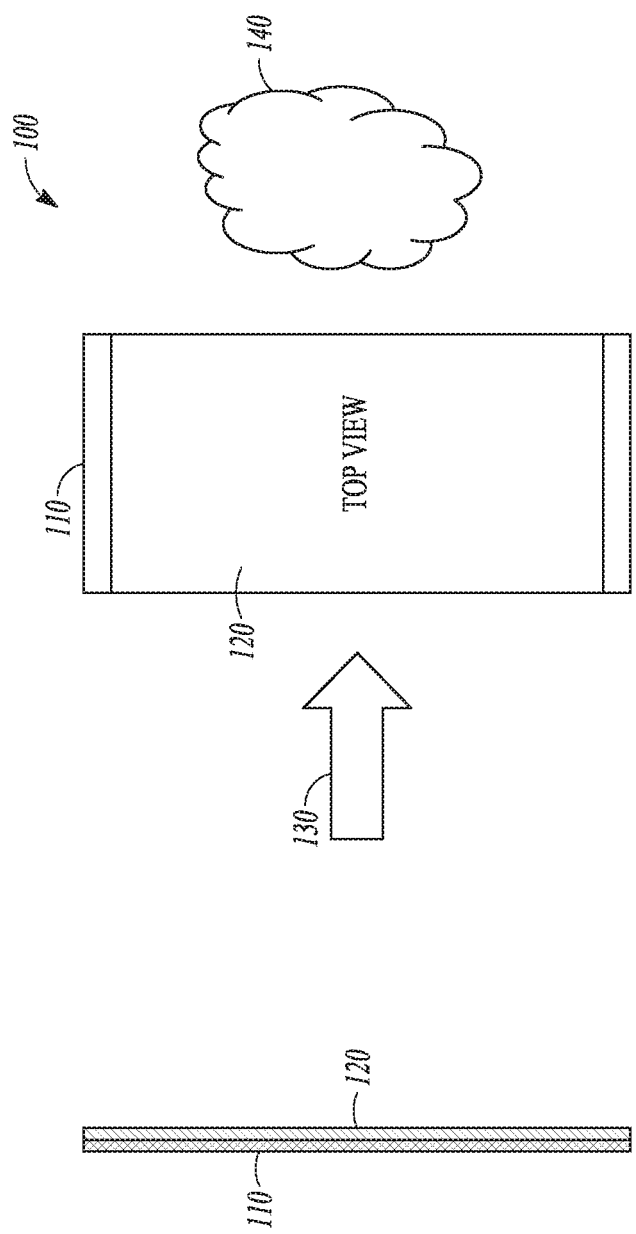
FIG. 1A is a side view of an example of a drug coated substrate in accordance with the present patent application.
FIG. 1B is a top view of the drug coated substrate of FIG. 1A.

The present application relates to methods of purifying at least one of THC and CBD from *cannabis*-containing compositions by heating the *cannabis*-containing compositions to vaporize at least one of THC and CBD and condensing the vapor onto a substrate to form a coated substrate comprising at least one of THC and CBD. The coated substrates can be converted into various three-dimensional structures configured for use as a drug delivery cartridge. The drug delivery cartridge can be heated up and air can pass through the cartridge, thus volatilizing the THC or CBD in the drug delivery cartridge such that the user can inhale the THC or CBD for a medicinal or therapeutic effect. The purity and ratios of THC and CBD in the drug delivery cartridge can be controlled based on the desired composition, and the quantities of THC and CBD can be controlled based on the desired dosage. Based on the process used to form the coated substrates, undesirable components in the *cannabis* are not included in the drug delivery cartridge. The drug delivery cartridges described herein can be used with various types of drug delivery devices to aid in inhalation of the THC or CBD.

The drug delivery cartridge can be a cylindrical structure extending in a longitudinal direction and formed from a substrate of an electrically conductive material. Electrodes can extend laterally across the substrate at respective longitudinal locations. The electrodes can each have an electrical resistance small enough to conduct current laterally along the substrate without heating the cylindrical structure. One or more substrate portions can have an electrical resistance sufficient to conduct current longitudinally between the electrodes and resistively heat the substrate portions. THC and/or CBD can be disposed on the one or more substrate portions and configured to volatilize in response to the resistive heating of the substrate portions. The cylindrical structure or other type of drug delivery cartridge can be used in various types of drug delivery systems.

As used herein, volatilize or volatilization can refer to vaporization of a component from a starting phase, either a liquid or a solid, to a gas phase. In an example, one or more components described herein may start as a solid and be heated such that the one or more components vaporize. The one or more components may transition directly from the solid to the gas phase, a sublimation process, or the one or more components may become a liquid and then vaporize to a gas. In an example, the one or more components described herein may be in a liquid form prior to heating. FIGS. 1A and 1B show side and top views of an example of a drug coated substrate 100 of the present disclosure. The drug coated substrate 100 can include a substrate component 110 onto which a drug component 120 can be deposited. The drug coated substrate 100 can be exposed to heated air 130, and the drug component 120 can be volatilized and entrained in the heated air 130 to form a heat released drug or HRD 140. The HRD 140 can then be ingested by a user to induce a medicinal or therapeutic effect on the user.

The substrate component 110 can be constructed from any naturally-occurring material or any man-made material, such as an FDA-approved polymer for the delivery of drugs, or any combination of naturally-occurring or man-made materials. The material selected for the substrate component 110 is inert at the heating temperatures described below for forming the coating on the substrate and the heating temperatures for later inhaling the one or more drug components from the coated substrate. In an example, the substrate component 110, can include, but is not limited to, materials where the substrate component 110 can be elastic, flexible, resilient, permanently deformable or plastically deformable.

In an example, the substrate component 110 can assume the form of any three dimensional structure, including, but not limited to, a sheet, a mesh, or any combination of three dimensional structures. Other types of structures can be employed without departing from the present subject matter. In an example, the substrate component 110 can be a sheet of polymer material. In an example, the substrate component 110 can be a sheet of aluminum mesh, a sheet of solid aluminum or a combination of both aluminum mesh and aluminum sheet. As used herein, the term aluminum can include all grades of aluminum and aluminum alloys. Materials suitable for use as the substrate component 110 are also described below in reference to FIG. 3.

As described further below, the substrate component 110 can be formed into a variety of three-dimensional shapes to form a drug delivery cartridge. In an example, the drug delivery cartridge can be designed to maximize the surface area of the drug component 120 exposed to the flow of heated air 130. In an example, the substrate component 110 can be shaped into forms including, but not limited to, a cone, a tube or tubular structure. As used here, a tubular structure can include any structure with an open cross-sectional area shape, a closed cross-sectional area shape, or a combination of open and closed cross-sectional area shapes. In an example, the cross-sectional area shapes can include, but are not limited to, circles, ovals, ellipses, squares, rectangles or other polygonal shapes. In an example, the cross-sectional area shapes can be open or closed shapes. Other types of structures can be employed without departing from the present subject matter.

The drug component 120 can include any volatilizable chemical or chemicals present in a raw material or a man-made material. In an example, the drug component 120 can include one or more active components for medicinal purposes or therapeutic effect. In an example, the drug component 120 can include one or more chemicals found in raw *cannabis*, including tetrahydrocannabinol, otherwise known as THC, or cannabidiol, otherwise known as CBD.

*Cannabis* material can exist in at least three distinct forms including, but not limited to, stem, resin (or hashish) and oil (or hash oil). In an example, the stem can include raw *cannabis* components such as stalks, leaves and flowers. As used herein, raw *cannabis* can refer to *cannabis* material that has been harvested but is otherwise unprocessed. In an example, the stem material can be shredded or chopped to increase the surface area of the stem material in preparation for purification. In an example, the resin can include kief, or the small particles of stem material that can be separated from the stem material by mechanical forces such as shaking. In an example, the kief can be compressed to form a solid for storage and later can be shredded or chopped to increase the surface area of the kief in preparation for purification. In an example, the oil can be obtained by solvent extraction treatments. Multiple references are made herein to starting with raw *cannabis*; it is recognized that any *cannabis*-containing composition can alternatively be used in the descriptions and examples below. Some of the processing steps, such as the separation or purification step, may vary depending on whether raw *cannabis* or an alternative form of a *cannabis*-containing composition is used.

Figure 2:
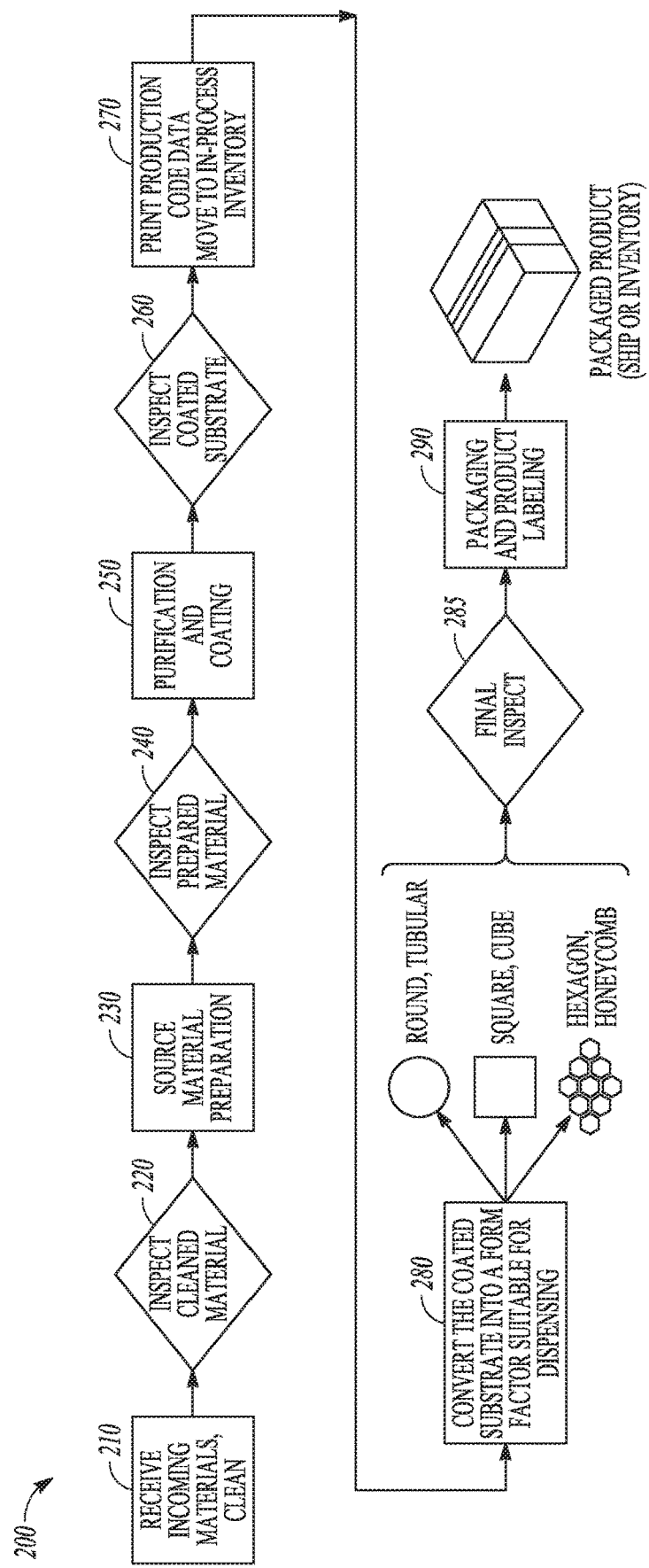
FIG. 2 is a block diagram of an example of a process for making a drug delivery cartridge in accordance with the present patent application.

FIG. 2 shows an example of a process 200 that can be used to form a drug delivery product, also referred to herein as a drug delivery cartridge. In an example, the drug delivery product includes at least one of THC and CBD. In the process 200, a pre-processing step 210 can include receiving source material, such as, for example, raw *cannabis*. In an example, the pre-processing step 210 can include collection of raw material from certified growers for use as source material and removal of undesirable organic and inorganic components from the source material. In an example, the source material can be a whole *cannabis* plant including the buds, leaves and stem.

A first inspection step 220 can include examination of the source material for general suitability in the process 200. In an example, source material that is diseased or not otherwise of a specified quality can be removed from the source material before further processing.

A source material preparation step 230 can further prepare the source material for later steps in the process 200. In an example, the source material preparation step 230 can include the use of equipment and methods to increase the surface area of the source material, such as by shredding or chopping, to aid in a purification process.

A second inspection step 240 can include examination of source material to ensure that the source material has been suitably processed. In an example, source material that has been improperly shredded or chopped may be rejected or redirected for further processing.

A purification and coating step 250 can include a process for separating the chemicals used to form the drug component 120 of FIG. 1 from the source material. In an example, the source material is raw *cannabis* and the one or more chemicals used to form the drug component 120 include at least one of THC and CBD. The purification in step 250 can include heating a *cannabis*-containing composition to volatilize at least one of THC and CBD from the *cannabis*-containing composition. Specific steps can depend on the form of the *cannabis*-containing composition. Under step 250, the volatilized chemicals can then be condensed onto a carrier material to form a drug coated substrate. In an example, the condensation of volatilized chemicals on a carrier material can be through absorption or adsorption of the volatilized chemicals.

A third inspection step 260 can include examination of the drug coated substrate for coating uniformity or other predetermined parameters.

A first post-processing step 270 can include identification and handling of the drug coated substrate. In an example, the drug coated substrate can be marked or labeled for quality assurance and material handling purposes, such as delivery of the drug coated substrate to inventory. In an example, steps 260 and 270 can be skipped and the coated substrate from step 250 can go directly to step 280 for converting.

A conversion step 280 can include transforming the drug coated substrate into form factors convenient for consumption by an individual user. In an example, the conversion step 280 can include converting the drug coated substrate into segments and forming the segments into drug delivery products or cartridges. In an example, the cartridge is constructed to maximize the surface area of the drug coated substrate available for volatilization while minimizing packaging volume of the cartridge. In an example, the cartridge can be of a generally tubular form and assume any cross-sectional shape without altering the effect of the cartridge. In an example, the cross-section shape can include, but is not limited to, a circle, a square, a hexagon, a polygon or any symmetric or non-symmetric cross-sectional profile. Other types of shapes can be employed without departing from the present subject matter.

A fourth inspection step 285 can include examination of the cartridges to ensure that the cartridges have been suitably processed. In an example, the fourth inspection step 285 can include examination of the user shapes for visual uniformity or other parameters.

A second post-processing step 290 can include packaging and labeling of the cartridges. In an example, each cartridge can be wrapped as an individual unit. In an example, individual units can be labeled for quality assurance and governmental tax purposes.

In an example, all the aforementioned steps of the process 200 can be subject to standard manufacturing control techniques.

Figure 3:
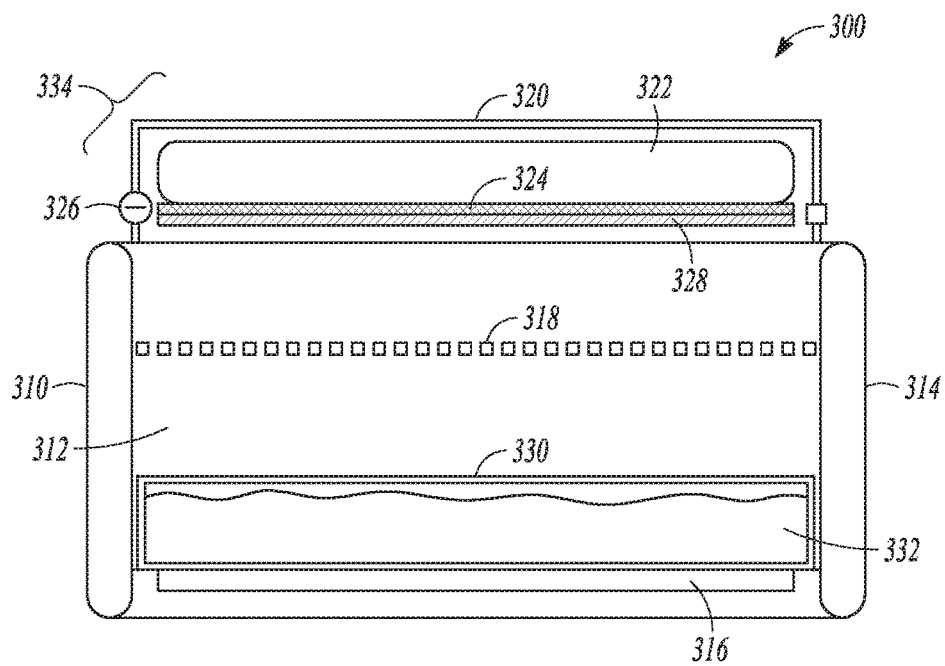
FIG. 3 is an example of a heating chamber for creating a coated substrate in accordance with the present patent application.

FIG. 3 shows an example of a heating chamber 300 of the present disclosure for use in a single sheet substrate coating process. The heating chamber 300 can include a container box 310 and a container cover 320 that can be removably attached to the container box 310. The container box 310 can include an interior surface 312, an exterior surface 314 and a controlled heat source 316 located along an interior surface 312 of the container box 310. A removable tray 330 to contain a source material 332 can be located against an interior surface 312 of the container box 310. A removable screen 318 can be located in the container box 310 between the removable tray 330 and the container cover 320 to contain source material 332.

The container cover 320 can include a hinge 326 to attach the container cover 320 to the container box 310 and a cooling bar 322 to which a substrate 324 can be located in close proximity or removably attached. In an example, the substrate 324 can be removably attached to the cooling bar 322 with clips or similar attachment aids.

The substrate 324 can be covered with a coating 328 of a drug component using, for example, a heating process. In an example, the drug component can include at least one of THC and CBD. The controlled heat source 316 can be initiated to heat the source material 332 to a selected temperature. Depending on the selected temperature, one or more chemicals can volatilize from the source material 332. The substrate 324 can be cooled through conduction (when in contact with the cooling bar 322) or radiation (when located in close proximity to the cooling bar 322) and the vapors generated during the heating process can condense onto the substrate 324 to form a coating 328 on the substrate 324. In an example, the one or more chemicals can be absorbed within the substrate 324. In an example, the one or more chemicals can be adsorbed onto the surface of the substrate 324. As used herein, a coated substrate 334 can refer to a combination of the substrate 324 and the coating 328 formed thereon.

In an example, the heating chamber 300 can be used to extract THC and CBD in the *cannabis*-containing composition. Using the steps above, the desirable components, THC and/or CBD, can be extracted and purified from the *cannabis*-containing composition by controlling the temperature in the heating chamber. As described further below, various drug coated substrates can be formed that have both THC and CBD, only THC, or only CBD, in purified form, and contain minimal to no undesirable components.

THC can volatilize in the heating chamber 300 before CBD based on volatilization temperatures of THC and CBD. Depending on a temperature that the *cannabis*-containing composition is heated to, THC can volatilize or THC and CBD can both volatilize. A rate of volatilization of each of THC and CBD can depend, in part, on the heating temperature and other conditions in the heating chamber 300, such as, for example, pressure. An exact temperature at which each of THC and CBD can volatilize is not necessarily precisely known and can depend, for example, on the surrounding conditions. In an example, a temperature of approximately 150-160° C. can be sufficient to volatilize THC and a temperature of approximately 180-200° C. can be sufficient to volatilize CBD.

A composition of the coated substrate 334, including a purity of the drug component, can be a function of the source material used in the heating process. In an example, the grade of *cannabis* used as the source material, such as the species and source of supply, can influence the composition of the coated substrate 334, including varying levels of THC and CBD. In an example, the pre-processing of the source material, such as the size of particle resulting from shredding and chopping of the source material, can influence the composition of the coated substrate 334. In an example, sampling can be performed on the source material to determine a composition of the source material. Specification parameters and standard processing control can be implemented for monitoring and controlling the composition of the source material and the coated substrate 334.

The composition of the coated substrate 334 can be a function of the control parameters used in the heating process. In an example, the temperature of the chamber, the total time the source material is exposed to the temperature of the chamber and the temperature of the cooling bar 324 can influence the coated substrate 334. In an example, these and other process parameters can be under standard processing control.

The substrate 324 can be constructed from any naturally-occurring material or any man-made material, such as an FDA-approved polymer for the delivery of drugs, or any combination of naturally-occurring or man-made materials.

The substrate 324 can be a pharmaceutically acceptable material or combination of materials, including natural and/or synthetic materials, which can capture the one or more chemicals in the drug component, such as, for example, THC or CBD. In an example, pharmaceutically acceptable materials for the substrate can include, but are not limited to, cellulosic materials, synthetically altered cellulosic materials, synthetic polymers, natural polymers or any material approved for pharmaceutical use by the United States Food and Drug Administration (FDA). In an example, the materials can be porous, micro-porous, adsorptive, absorptive or include a combination of adsorptive and absorptive properties. In an example, the substrate can be stable and non-degrading at temperatures well above the volatilization temperatures of THC and CBD. In an example, the substrate 324 can comprise an aluminum or aluminum alloy.

Figure 4:
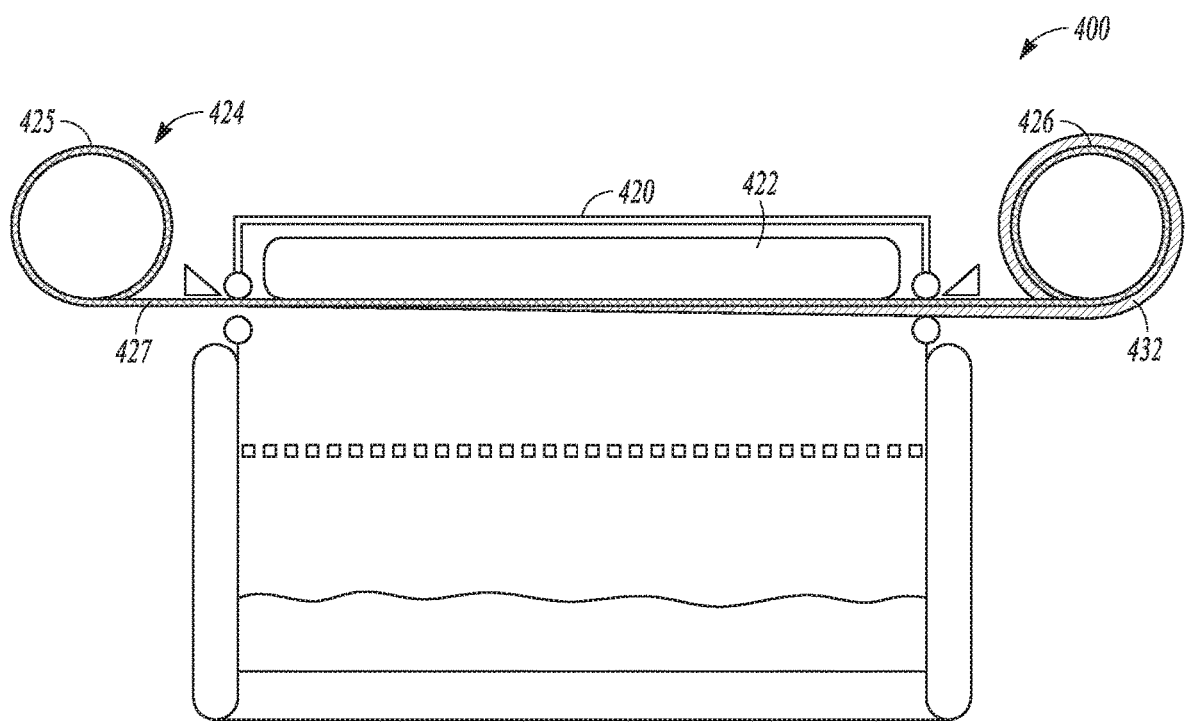
FIG. 4 is an example of a heating chamber having a continuous substrate coating process in accordance with the present patent application.

FIG. 4 shows an example of a heating chamber 400 of the present disclosure for use in a continuous sheet substrate coating process. The heating chamber 400 can include many of the same elements as the heating chamber 300 of FIG. 3, but instead of being a patch process can include additional features to enable a continuous process. The container cover 420 can include a roller take-up mechanism 424. In an example, the roller take-up mechanism 424 can include a source spool mechanism 425, a receiving spool mechanism 426 and a flexible substrate 427 extending from the source spool mechanism 425 to the receiving spool mechanism 426 and located in close proximity to the cooling bar 422. In an example, the source spool mechanism 425 can include a spindle and bearings to support the source spool and a motor attached to the source spool for tensioning of the flexible substrate 427. In an example, the receiving spool mechanism 426 can include a spindle and bearings to support the receiving spool and a motor attached to the receiving spool to draw the flexible substrate 427 across the cooling bar 422. During the heating process, the receiving spool mechanism 426 can draw the flexible substrate 427 across the cooling bar 422 so that the one or more chemicals condenses on one side of the flexible substrate 427 to form a continuous coating 432 on the flexible substrate 427.

In an example, the roller take-up mechanism 424 can be controlled to perform continuous deposition processing of the flexible substrate 427. In an example, the roller take-up mechanism 424 can be controlled to perform multi-batch deposition processing of the flexible substrate 427. Other designs can be used as an alternative to or in addition to the mechanisms 424 and 426 for enabling a continuous process.

Figure 5:
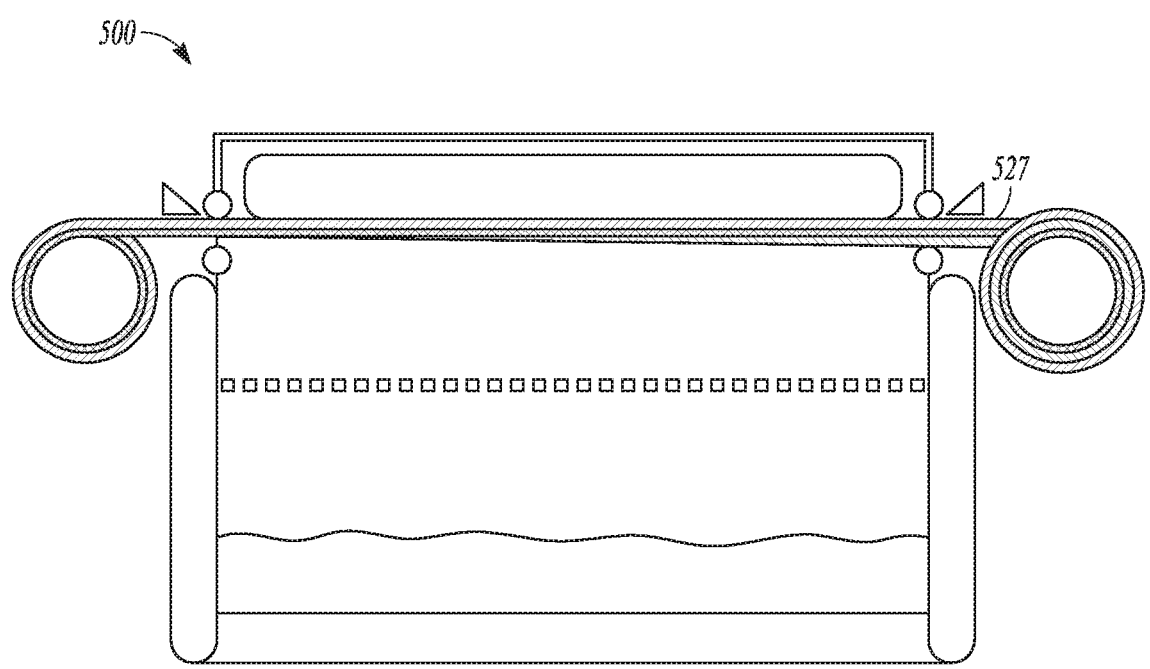
FIG. 5 is an example of a heating chamber having a double-sided, continuous substrate coating process in accordance with the present patent application.

FIG. 5 shows an example heating chamber 500 of the present disclosure for use in a double-sided, continuous sheet substrate coating process. The heating chamber 500 can include many of the same elements as the heating chambers 300 and 400 of FIGS. 3 and 4, respectively. In an example, after one side of the flexible substrate 527 has been coated in either a multi-batch or continuous deposition process, the uncoated side of the flexible substrate 527 can be subsequently coated by a multi-batch or continuous deposition process.

Figure 6:
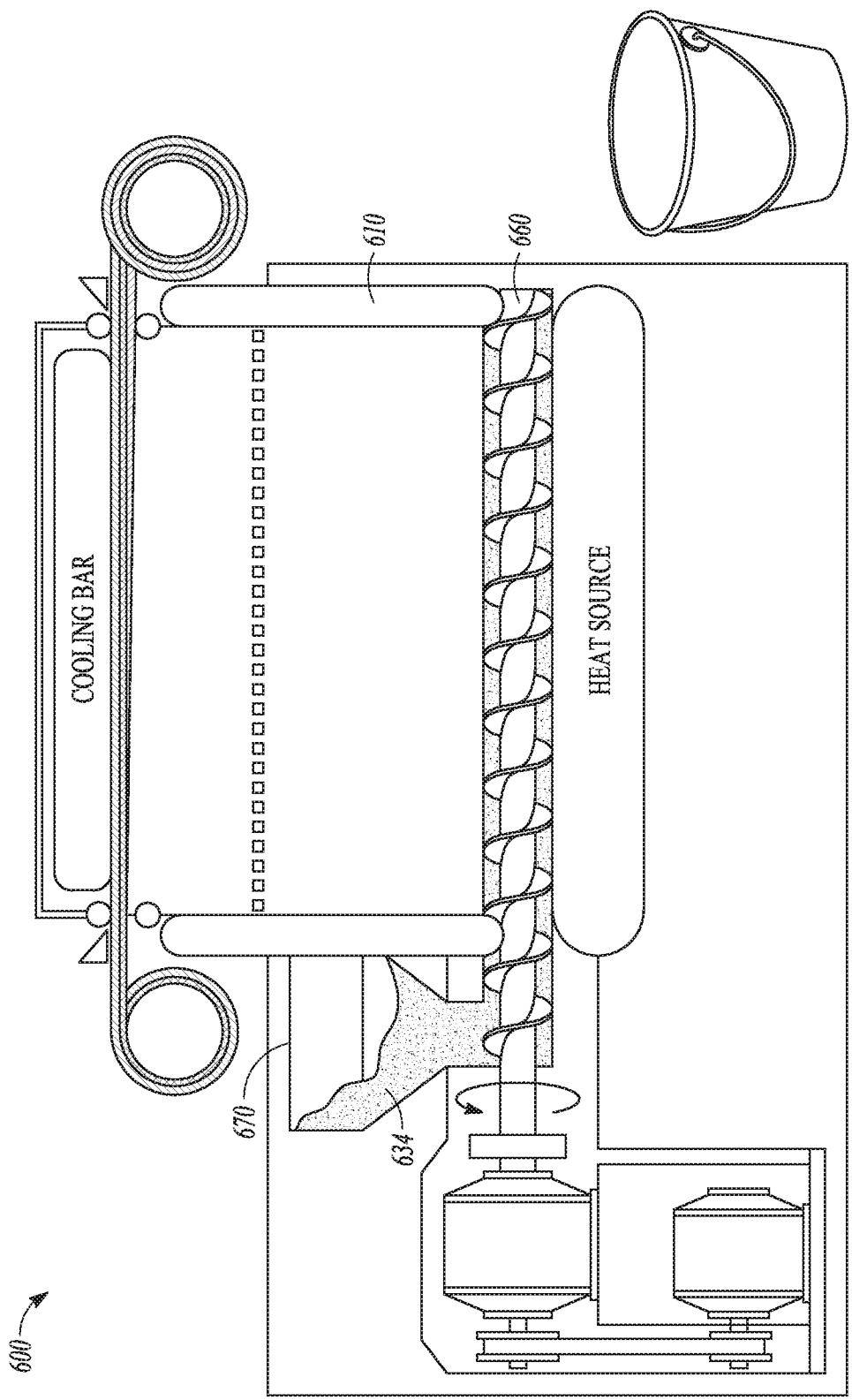
FIG. 6 is an example of a heating chamber having a double-sided, continuous substrate coating process with a source material feed system in accordance with the present patent application.

FIG. 6 shows an example heating chamber 600 of the present disclosure for use in a double-sided, continuous sheet substrate coating process with a continuous source material feed system. In an example, a screw conveyor 660 can move source material 634 into the container box 610 for heating and volatilization. In an example, the source material 634 can be deposited into a hopper 670 to supply the screw conveyor 660.

In an example, any of the heating chambers described above can be part of a mobile process such that the purification and coating processes can be done at or near the origin of the source material. In an example in which the source material is raw *cannabis*, the purification and coating processes can be contained or stored within a transportation device such that these steps can be performed at or near where the raw *cannabis* is grown.

In an example, a batch process similar to the heating chamber 300 of FIG. 3 can be used to sample source material and determine its composition, to determine, for example, levels of THC and CBD in the source material.

The heating chambers and processes described above in reference to FIGS. 3-6 are an example of a separation process for separating one or more components from the *cannabis*-containing composition. Other known processes may be used, such as, for example, a fractional distillation process. The particular process used for separating the desired components from the source material can depend, in part, on the composition and form (solid, liquid, etc.) of the source material, the volume of coated substrate to be produced, the time for production, technical expertise of the users, equipment availability and budget, and the cost of implementation.

By starting with raw *cannabis* or a *cannabis*-containing composition, one or more components can be extracted from the *cannabis* and purified by volatilizing the one or more components and coating the one or more components onto a substrate. Isolation and purity of the one or more components can be controlled through the volatilization and coating steps. The coated substrate can include more than one coating layer. In an example, a CBD rich layer can be coated over a THC rich layer. In an example, a THC rich layer can be coated on one side of the substrate and a CBD rich layer can be coated on the other side of the substrate. In an example, a CBD rich layer and minimal to no THC can be coated onto a substrate. In an example, a THC rich layer and minimal to no CBD can be coated onto a substrate. In an example, multiple substrates, each having one or more coating layers, can be used together to provide one or more drug components.

In an example, the purification and coating processes described above can include replenishing or replacing the source material after a period of time in order to vaporize an additional amount of the one or more components. In an example, the purification and coating processes described above can include processing the coated substrate into smaller pieces to increase a total surface area and then heating the pieces of coated substrate such that the at least one of THC and CBD in the coated substrate are vaporized and then condensed onto a new substrate. This can be used to further purify the at least one of THC and CBD in the coated substrate and can be repeated until a desired purity of the at least one of THC and CBD is achieved.

The heating chambers described above can be used to heat the *cannabis*-containing composition to any given temperature. The particular temperature or temperature range selected can depend on multiple factors, including, for example, a particular composition of the raw *cannabis* or the desired composition of the coated substrate. In an example, the heating chamber can be configured to heat the *cannabis*-containing composition to a temperature ranging between approximately 90-200° C. The temperature can be incrementally increased starting, for example, at approximately 50° C. In an example, a process for forming the coated substrate can include such a step-wise temperature increase, for example at increments of 10° C., using fractional distillation. Samples can be collected of the vapors after deposition, at all or some of the temperature intervals, to analyze the fractions and determine the composition of the coating. Based on the results, the temperature range sufficient for volatilization can be determined or adjusted based on the desired composition of the coating. It is recognized that the temperature range can depend on the starting material and how tightly the composition of the coating is to be controlled. The composition of the starting material can vary from batch to batch and can depend, for example, on where and how the raw *cannabis* is grown, and cleaning of the raw *cannabis*, or other preparation steps, prior to processing.

Given a differential of the volatilization temperatures of THC and CBD, different approaches can be used to isolate THC from CBD and vice-versa. In an example, the *cannabis*-containing composition can be heated to approximately 150-160° C. to volatilize THC and form a coated substrate that is rich in THC. In an example, the *cannabis*-containing composition can be heated to a temperature of approximately 175-190° C. to volatilize THC and CBD simultaneously. In such an example, a particular composition of the coated substrate obtained can depend, in part, on the exact temperature selected, as well as the starting ratios of THC and CBD in the *cannabis*-containing composition. It is recognized that other temperature ranges can be used that are sufficient for volatilizing one or both of THC and CBD.

In an example, if a coated substrate rich in CBD and not THC is desired, a two step process can be used. In a first step, the *cannabis*-containing composition can be heated to a first temperature sufficient to volatilize THC, but little to no CBD. Thus the coating deposited on a first substrate can be rich in THC. Depending on a length of heating in the first step, little to no THC can remain in the *cannabis*-containing composition after the first step is complete. In a second step, the *cannabis*-containing composition can be heated to a second temperature greater than the first temperature and sufficient to volatilize CBD. CBD can then be deposited onto a second substrate to form a coating rich in CBD. In other examples, the THC rich layer and the CBD rich layer can be coated as first and second coatings on a single substrate.

It may be desirable not to heat the *cannabis*-containing composition above a particular temperature in order to avoid volatilization of other undesirable components in addition to THC and CBD that are present in and able to volatilize from the *cannabis*-containing composition. In an example, a maximum heating temperature can be approximately 190-200° C. to avoid or minimize volatilization of these other components.

As described above, further processing can be performed on one or both of the first and second coated substrates to further increase a purity of the CBD or THC in the coating. Depending on the particular temperature selected, as well as the composition of the source material and other conditions in the heating chamber, the coated substrate can have varying ratios of THC to CBD.

An amount of the one or more drug components in the coated substrates can be determined as part of the process for forming the coated substrate and the drug delivery cartridges described below. As described above, process control methods can be implemented to control, for example, a thickness of the coating on the substrate. Based on sampling of the source material, a composition of the coating on the substrate can also be determined. Other known techniques can be used to determine a composition of the coating on the substrate. As such, an amount of the one or more drug components, such as, for example, THC and CBD, can be determined per unit area of the coated substrate. This can be used to determine a surface area of the drug delivery cartridge if there is a specified level of the one or more drug components in the drug delivery cartridge. Similarly, if the surface area of the drug delivery cartridge is specified, the thickness of the coating on the substrate can be adjusted in order to meet a specified level of the one or more drug components in the drug delivery cartridge. The methods described herein for forming the coated substrates and the drug delivery cartridges can be used to effectively and accurately determine a composition and level of the one or more drug components, which can be used for dosage control.

Coated substrates as described herein containing one or more drug components can be used to form a three-dimensional structure configured for use as a drug delivery product. In an example, a coated substrate can be used as a drug delivery cartridge in a delivery device. As used herein, a drug delivery cartridge can refer to a replaceable element in a drug delivery system that is slowly depleted of one or more drug components as a consequence of continued use or intervals of use. The drug delivery cartridge can be replaced for continued use of the drug delivery system. In an example, drug delivery cartridges can be designed to maximize surface area exposed to an air flow while minimizing package volume.

Coated substrates can take many structural forms. In an example, coated substrates can include, but are not limited to, cubes, cones, parallelepipeds, or other three-dimensional shapes. In an example, a coated substrate can be in the form of a sheet. As used herein, a sheet can be any three-dimensional structure defined by a first dimension, a second dimension and a third dimension where the first dimension is much smaller than the second and third dimensions. In an example, a sheet can be generally rectangular in shape with a first end and a second end opposite the first end.

Figure 7A:
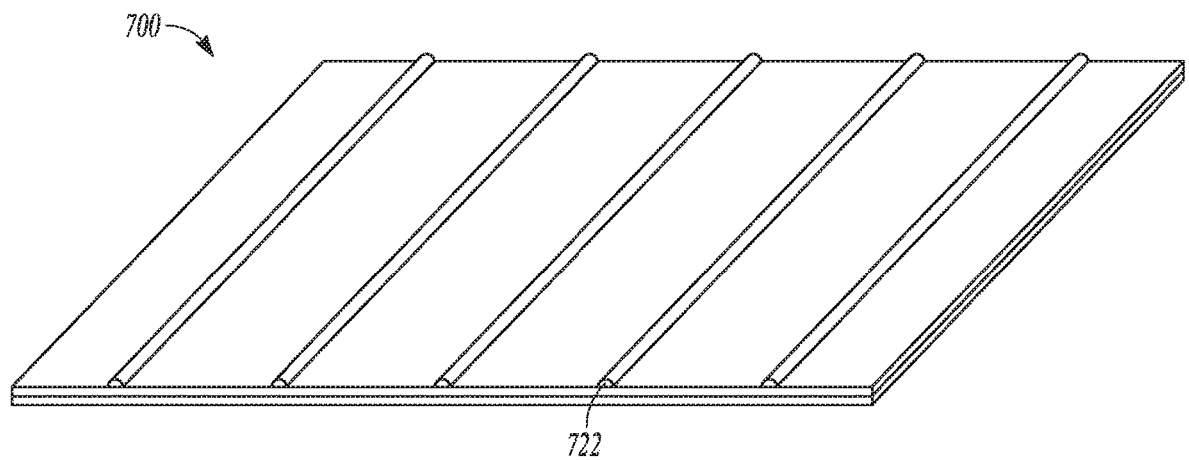
FIG. 7A is an example of a drug coated substrate in accordance with the present patent application.
Figure 7B:
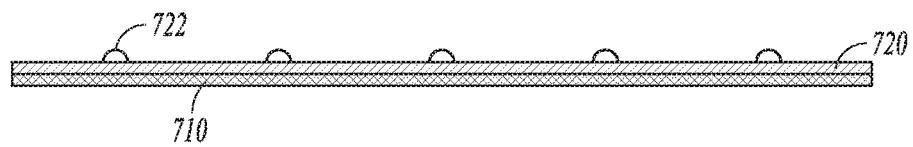
FIG. 7B is a cross-section view of the drug coated substrate of FIG. 7A.

FIGS. 7A and 7B show an example of a drug coated substrate 700 of the present disclosure which can be formed using the techniques described above or generally known in the art for extracting and purifying one or more drug components and coating the one or more drug components on a substrate. The drug coated substrate 700 can include a substrate component 710, a drug component 720 coated on the substrate component 710 and spacers 722 located on the substrate component 710 or the drug component 720. In an example, the spacers 722 can be located on the substrate component 710 before the substrate component 710 is coated. In an example, the spacers 722 can be located on the drug component 720 after the substrate component 710 is coated.

Figure 7C:
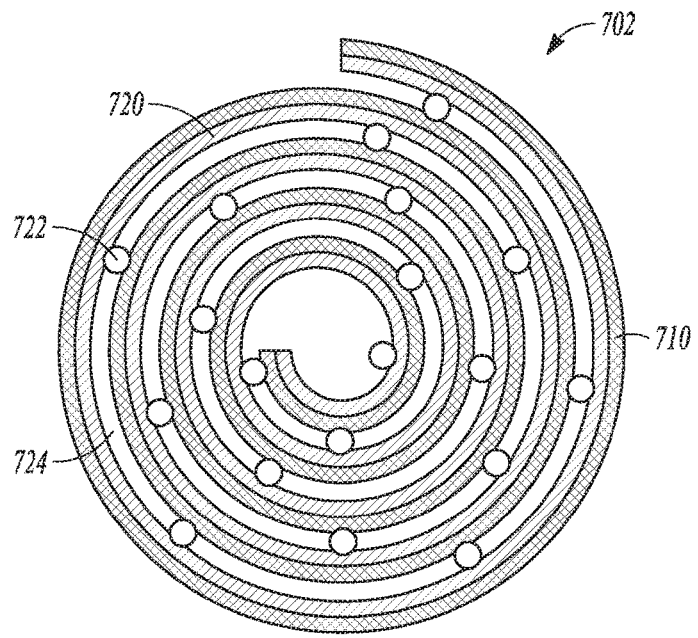
FIG. 7C is an example of a drug delivery cartridge formed from the drug coated substrate of FIG. 7A, in accordance with the present patent application.

FIG. 7C shows an example where the drug coated substrate 700 can be converted into a three-dimensional structure configured for use as a drug delivery cartridge 702. In an example, the drug coated substrate 700 can be rolled into a spirally wound cylindrical shape to form the drug delivery cartridge 702. In an example, the plurality of spacers 722 can be used as a structural element to maintain a channel 724 between layers of the drug delivery cartridge 702 to allow for the passage of heated air. The drug delivery cartridge 702 can include any number of layers.

The drug delivery cartridge 702 can be used with a drug delivery device, an example of which is described below and shown in FIG. 17. In an example, the drug delivery device can include, but is not limited to a vaporizer, an e-cigarette, a bong or a water pipe. Alternatively, the drug delivery cartridge 702 can be used by directly applying heated air to the drug delivery cartridge 702 to volatilize the drug from the drug delivery cartridge 702. In an example, heated air can be directly applied to the drug delivery cartridge 702 by any heating process or heating device that can include, but is not limited to, an e-cigarette, a bong, a water pipe and a vaporizer device. In an example, heated air can be directed through the channel 724 to volatilize the drug from the drug delivery cartridge 702.

Figure 8:
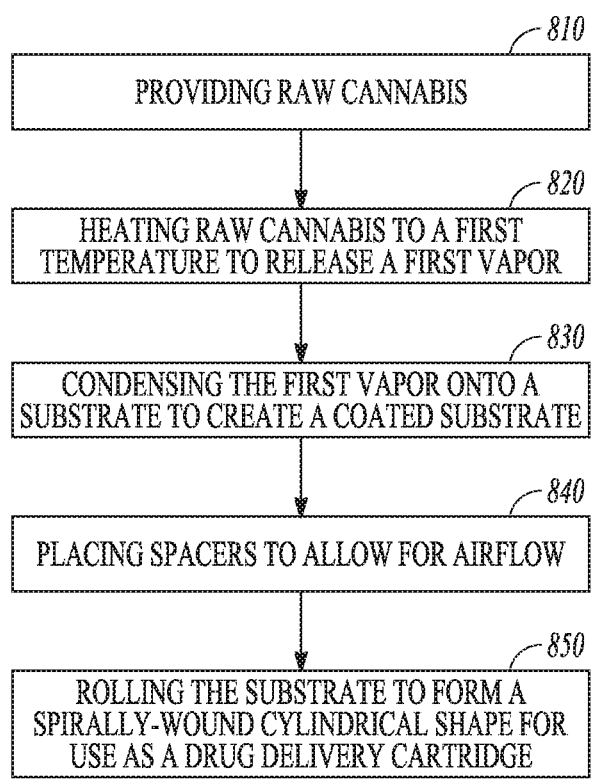
FIG. 8 is a block diagram of an example of a process to construct a drug delivery cartridge having a spirally wound cylindrical shape, in accordance with the present patent application.

FIG. 8 shows a flow chart of an example process to construct a spirally wound cylindrical shape, similar to the cartridge 702 of FIG. 7C. In an example, step 810 can include providing a supply of raw *cannabis*; step 820 can include heating the raw *cannabis* to a first temperature to release a first vapor; step 830 can include condensing the first vapor onto a substrate to create a coated substrate; step 840 can include placing spacers on the coated substrate to allow for airflow through the cartridge; step 850 can include rolling the coated substrate to form a spirally-wound cylindrical shape configured for use as a drug delivery cartridge.

Figure 9:
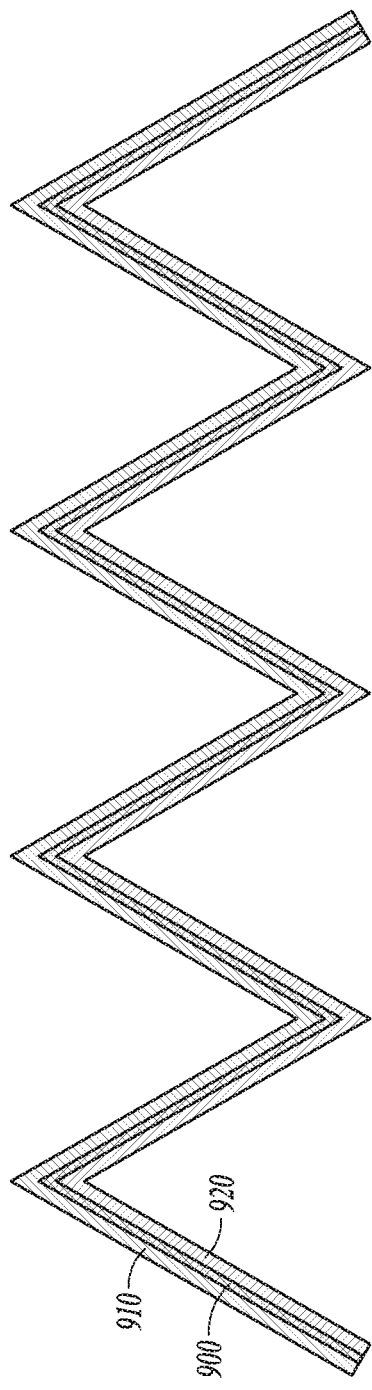
FIG. 9 is an example of a drug delivery cartridge in accordance with the present patent application.

FIG. 9 shows an example of a coated substrate shaped in a saw-tooth, zig-zag, or accordion configuration. In an example, the saw-tooth coated substrate 900 includes a first coating 910 where the first coating 910 can be one of THC or CBD. In an example, the saw-tooth coated substrate 900 includes a second coating 920 where the coating 920 can be one of THC or CBD.

Figure 10:
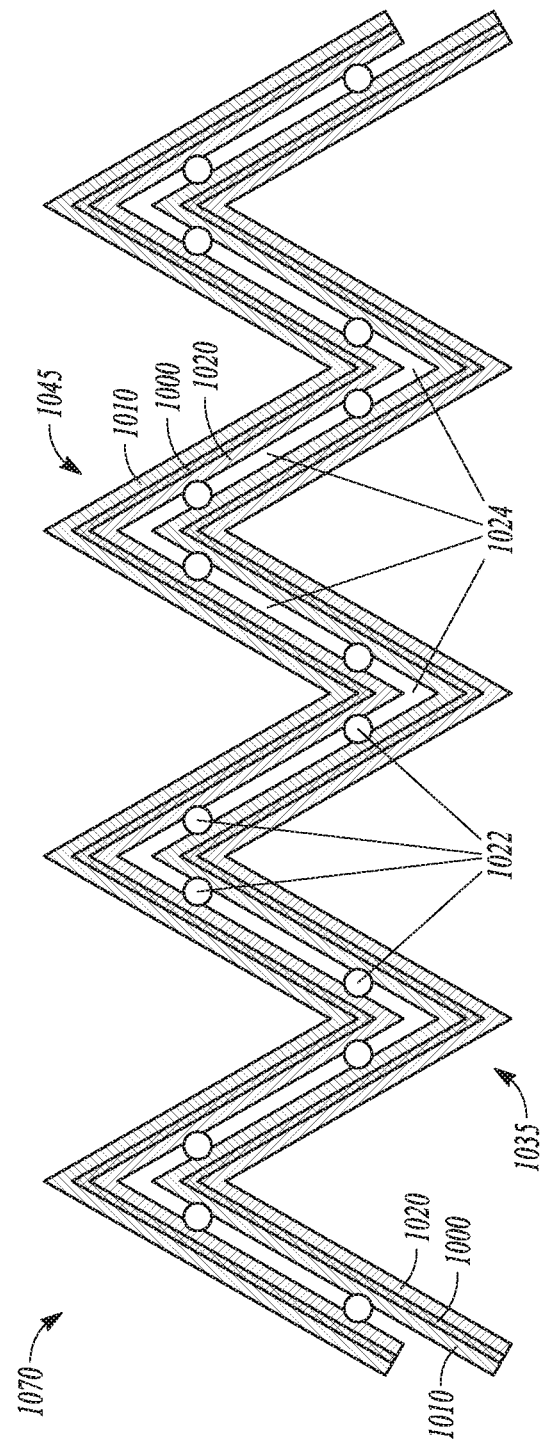
FIG. 10 is an example of a drug delivery cartridge having multiple layers of coated substrates, in accordance with the present patent application.

FIG. 10 shows an example of a two-substrate assembly 1070 where a first saw-tooth coated substrate 1035 and a second saw-tooth coated substrate 1045 can be stacked for use as a drug delivery cartridge. In an example, a plurality of spacers 1022 can be used as structural elements to maintain a plurality of channels 1024 between the first saw-tooth coated substrate 1035 and the second saw-tooth coated substrate 1045 to allow for the passage of heated air. In an example, the two-substrate assembly 1070 can be stacked so that the first coating 1010 of the first saw-tooth coated substrate 1035 can face the second coating 1020 of the second saw-tooth coated substrate 1045. In an example, a plurality of two substrate assembly 1070 can be stacked for use as a drug delivery cartridge.

Figure 11:
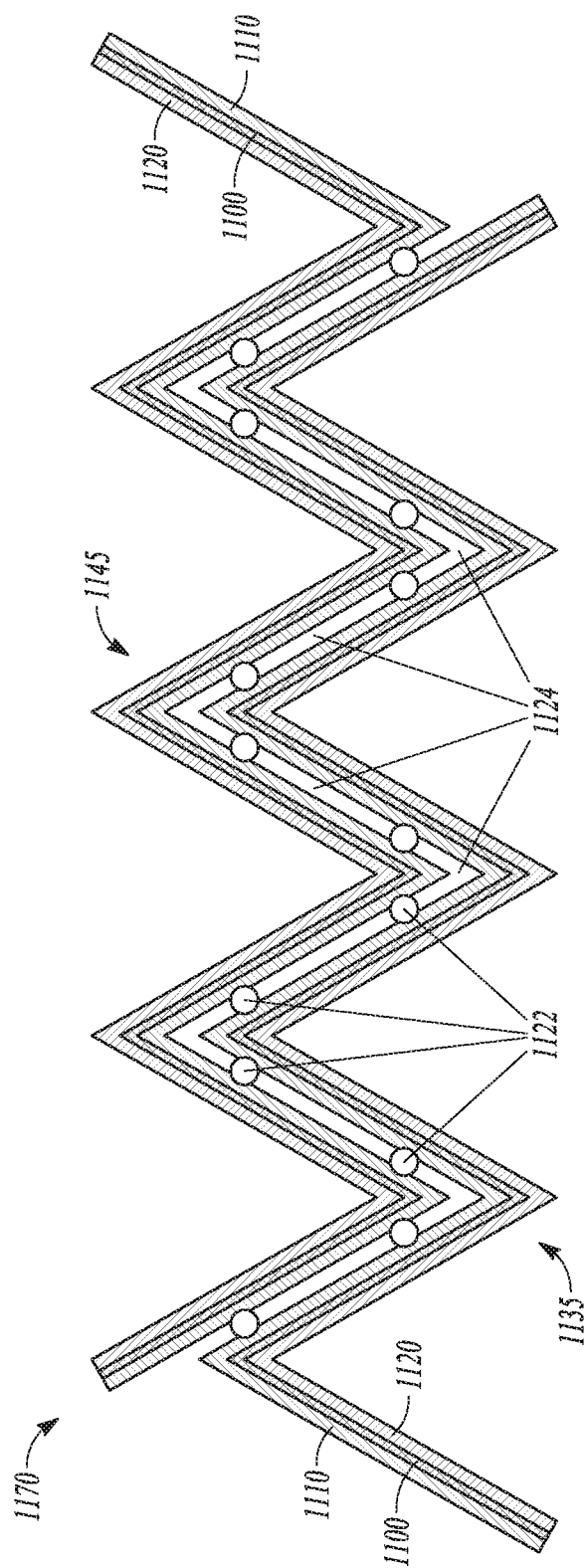
FIG. 11 is an example of a drug delivery cartridge having multiple layers of coated substrates, in accordance with the present patent application.

FIG. 11 shows an example of a two-substrate assembly 1170 where the first coating 1110 of a first saw-tooth coated substrate 1135 can face the first coating 1110 of a second saw-tooth coated substrate 1145. In an example, a plurality of two-substrate assembly 1170 can be stacked for use as a drug delivery cartridge.

Figure 12:
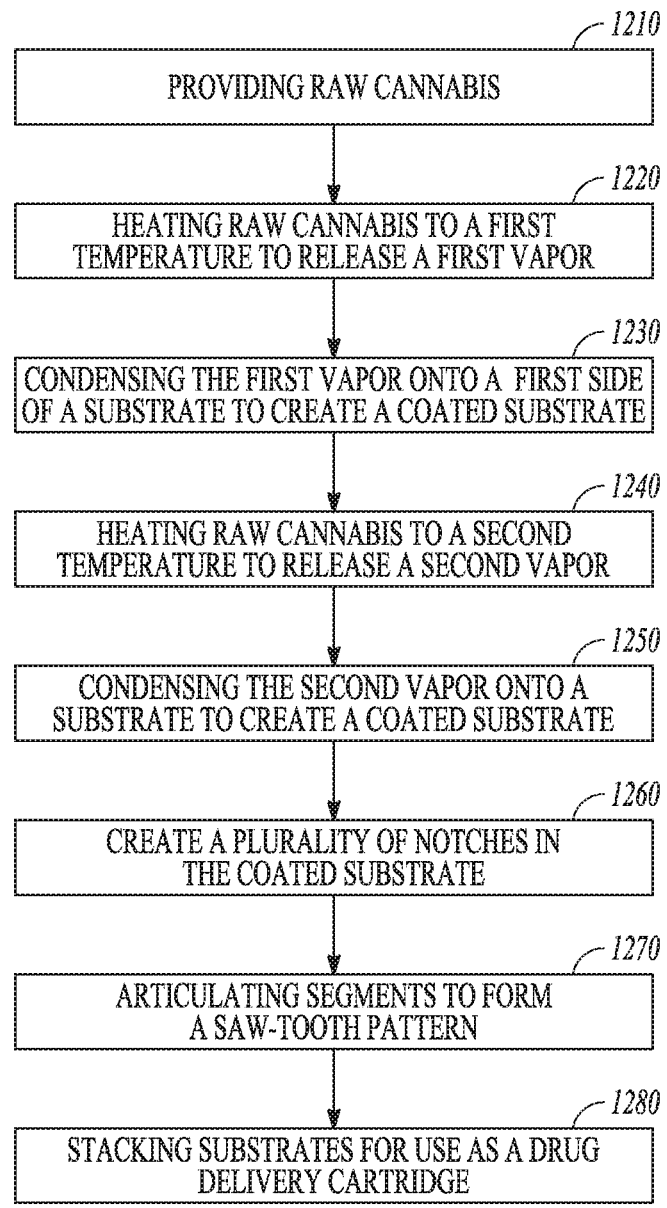
FIG. 12 is a block diagram of an example of a process to construct a drug delivery cartridge in accordance with the present patent application.

FIG. 12 shows an example of a process to construct a saw-toothed drug delivery cartridge. In an example, step 1210 can include providing a supply of raw *cannabis*; step 1220 can include heating the raw *cannabis* to a first temperature to release a first vapor; step 1230 can include condensing the first vapor onto a first side of a substrate; step 1240 can include heating the raw *cannabis* to a second temperature to release a second vapor; step 1250 can include condensing the second vapor onto a second side of the substrate; step 1260 can include creating a plurality of notches in the coated substrate; step 1270 can include articulating the segments to form a saw-tooth pattern and step 1280 can include stacking the substrate for use as a drug delivery cartridge. The process of FIG. 12 can be modified to incorporate the multiple substrate assemblies shown in FIGS. 10 and 11.

Figure 13A:
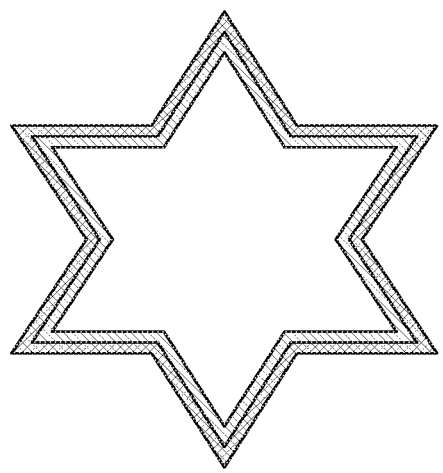
FIG. 13A is a top view of an example of a polygonal drug delivery cartridge in accordance with the present patent application.
Figure 13B:
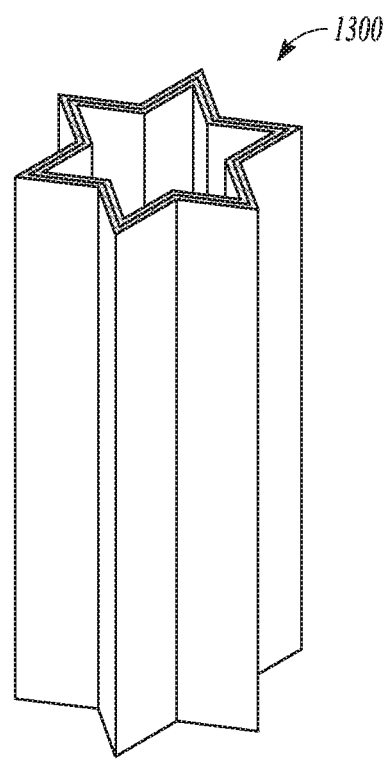
FIG. 13B is a perspective view of the polygonal drug delivery cartridge of FIG. 13A.

FIGS. 13A and 13B show top and side views, respectively, of an example of a polygonal drug delivery cartridge 1300. In an example, the cross-sectional shape of the polygonal drug delivery cartridge can include, but is not limited to, a three-side cross-section, a four-sided cross-section or an "n"-sided cross-section where "n" can be any number equal to or greater than 3.

Figure 13C:
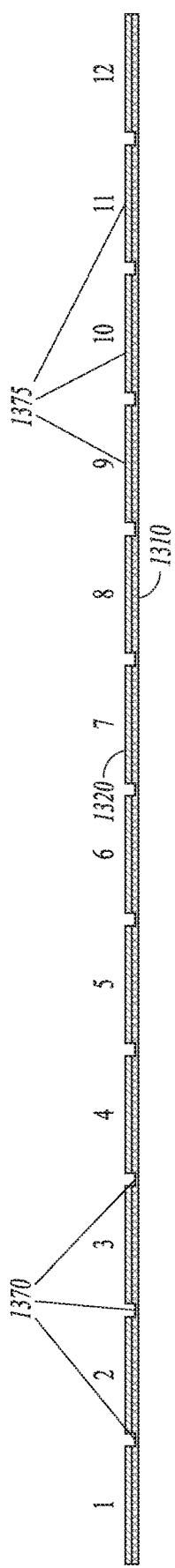
FIG. 13C is a side view of the coated substrate of the drug delivery cartridge of FIGS. 13A and 13B prior to forming the polygonal shape.
Figure 13D:
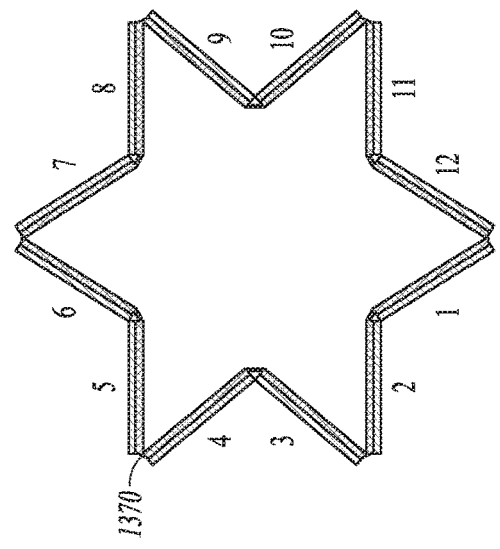
FIG. 13D is a cross-section view of the drug delivery cartridge of FIGS. 13A and 13B as assembled from the coated substrate shown in FIG. 13C.

FIG. 13C shows notches 1370 formed in the substrate 1310 and the coating 1320 that can allow a segment 1375 to articulate with respect to an adjacent segment 1375. As used herein, a segment 1375 is the portion of the substrate 1310 and coating 1320 located between two notches 1370. FIG. 13D shows the drug delivery cartridge 1300 as assembled from the coated substrate of FIG. 13C. FIG. 13D illustrates how each segment 1375 of FIG. 13C is configured in the assembled cartridge 1300 and a notch 1370 is located between each adjacent pair of segments 1375.

Figure 14:
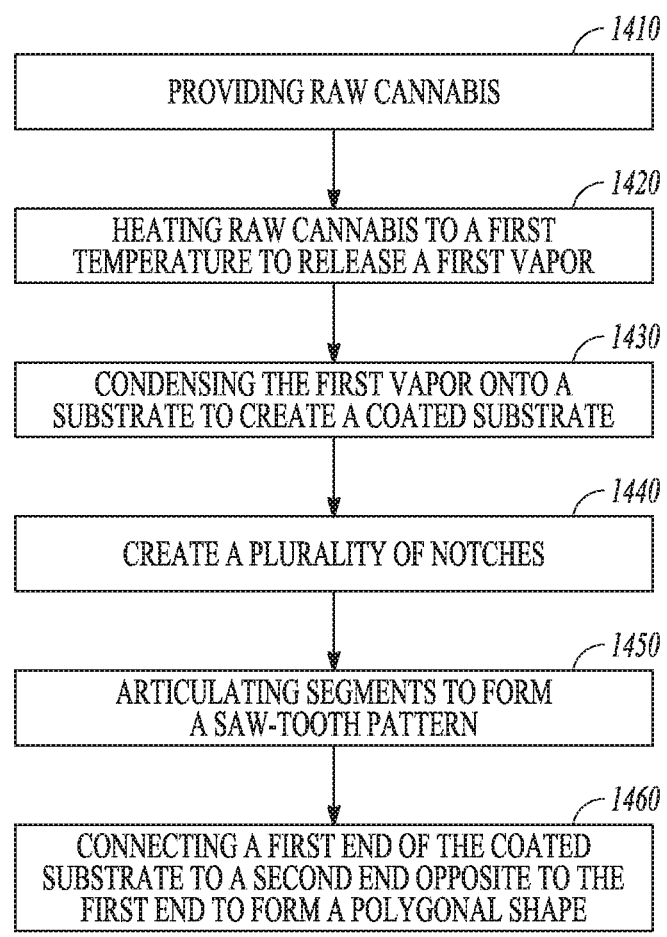
FIG. 14 is a block diagram of an example of a process to construct a polygonal drug delivery cartridge in accordance with the present patent application.

FIG. 14 shows an example of a process to construct a closed polygonal shaped drug delivery cartridge similar to the star-shaped cartridge 1300 of FIG. 13. In an example, step 1410 can include providing a supply of raw *cannabis*; step 1420 can include heating the raw *cannabis* to a first temperature to release a first vapor; step 1430 can include condensing the first vapor onto a substrate to create a coated substrate; step 1440 can include creating a plurality of notches and step 1450 can include articulating the segments to form a saw-tooth pattern; and step 1460 can include connecting the first end to the second end to form a polygonal shape. In an example, step 1460 can include manipulating the segments to align the segments in a desired orientation relative to one another.

Other shapes can be used for a drug delivery cartridge. Any of the examples described and shown in FIGS. 7C, 9, 10, 11 and 13A-13C can include additional layers of substrate and each layer of substrate can include one or more coating layers. As stated above in reference to FIG. 7C, the drug delivery cartridges described herein can be used alone or in combination with a drug delivery device. Each drug delivery cartridge can be designed such that heated air can be passed through the cartridge and one or more drug components can be volatilized and inhaled by a user.

Dimensions of any of the drug delivery cartridges described herein can depend, in part, on whether a drug delivery device is intended to be used with the cartridge and a particular design of the drug delivery device. These dimensions can include a length, width and overall shape of the drug delivery cartridge and can depend on the length and width of the coated substrate used to form the drug delivery cartridge. The dimensions of the drug delivery cartridge can also depend, in part, on an amount of the one or more drug components in the drug delivery cartridge and an intended dosage of the one or more drug components.

Figure 15:
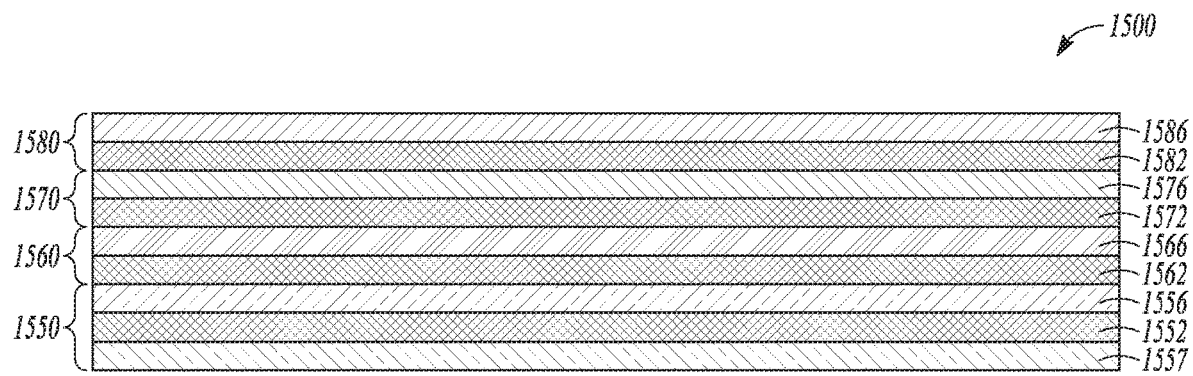
FIG. 15 is a cross-section view of an example of a multi-layer substrate in accordance with the present patent application.

FIG. 15 shows a cross-section view of an example of an assembly 1500 comprising multiple layers of coated substrates. In an example, an active drug layer 1550 can include a substrate 1552 with a first surface and a second surface where a THC coating 1556 can be applied to the first surface and a CBD coating 1557 can be applied to the second surface. In an example, a taste layer 1560 can include a substrate 1562 having a taste coating 1566 applied to the substrate 1562 to enhance the user ingestion experience. In an example, the taste coating 1566 can include a flavoring that can include, but is not limited to, fresh mint. In an example, an enhancement layer 1570 can include a substrate 1572 having an enhancement coating 1576 applied to the substrate 1572 where the enhancement coating 1576 can include at least a second compound that can augment the therapeutic effect of the THC or CBD. In an example, the second compound can include, for example, an opiate. In an example, an amelioration layer 1580 can include a substrate 1582 having an amelioration coating 1586 applied to the substrate 1582 where the amelioration coating 1586 can include at least a third compound that can minimize any undesirable side effects of THC or CBD, if applicable. In an example, the active drug layer 1550, the taste layer 1560, the enhancement layer 1570 and the amelioration layer 1580 can be assembled together or in any permutation. In an example, the assembly 1500 can be converted into a three-dimensional structure for use as a drug delivery cartridge as described above. In other examples, an assembly, can include any number and combination of layers depending on desired properties of the assembly. In an example, spacers similar to the spacers 722 shown in FIGS. 7A and 7B can be placed between each layer prior to forming the three-dimensional structure to allow for the passage of air between the layers.

Figure 16:
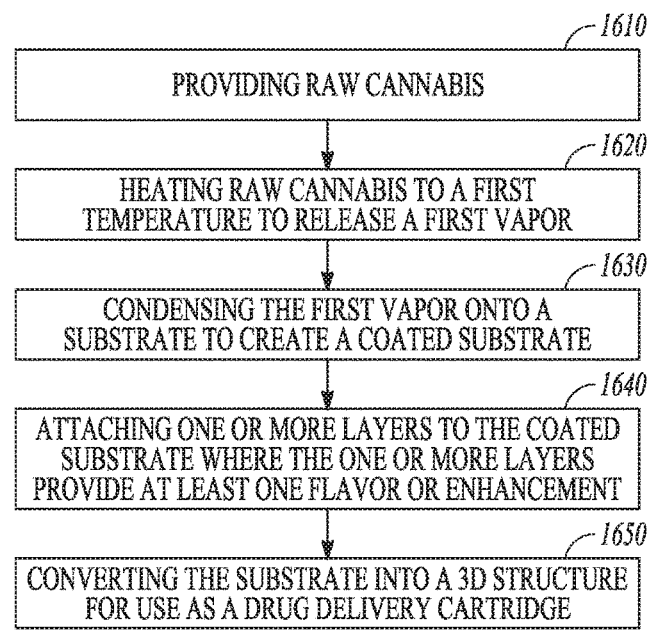
FIG. 16 is a block diagram of an example of a process used to make a drug delivery cartridge having two or more layers, in accordance with the present patent application.

FIG. 16 shows an example of a process used to make a drug delivery cartridge where the coated substrate includes two or more layers where at least one provides flavor or enhancement. In an example, step 1610 can include providing a supply of raw *cannabis*; step 1620 can include heating the raw *cannabis* to a first temperature to release a first vapor; step 1630 can include condensing the first vapor onto a substrate to create a coated substrate; step 1640 can include attaching one or more layers to the coated substrate where the one or more layers provide at least one of flavor or enhancement of the at least one of THC and CBD, and step 1650 can include converting the substrate into a three-dimensional structure for use as a drug delivery cartridge. In an example, an additional step can be performed between steps 1630 and 1640 which can include heating the raw *cannabis* to a second temperature to release a second vapor, thus creating a second coating on the coated substrate, as described above.

As described above in reference to the coated substrates, a composition and amount of the one or more drug components in the drug delivery cartridge can be determined and controlled, which can be used for dosage control of the drug(s). In an example, the drug delivery cartridges can contain a predetermined quantity of THC or CBD and can be designed as single dosage or multi-dosage cartridges. Using the control parameters described above, a quantity of THC or CBD in the drug delivery cartridge can vary depending, for example, on the intended use of the THC or CBD.

A drug delivery cartridge can cooperate with a drug delivery device that supplies a volatilizing heat source to deliver the one or more drug components in the drug delivery cartridge to a user. In an example, the drug delivery device can include, but is not limited to, an e-cigarette, a bong, a water pipe and a vaporizer.

Figure 17:
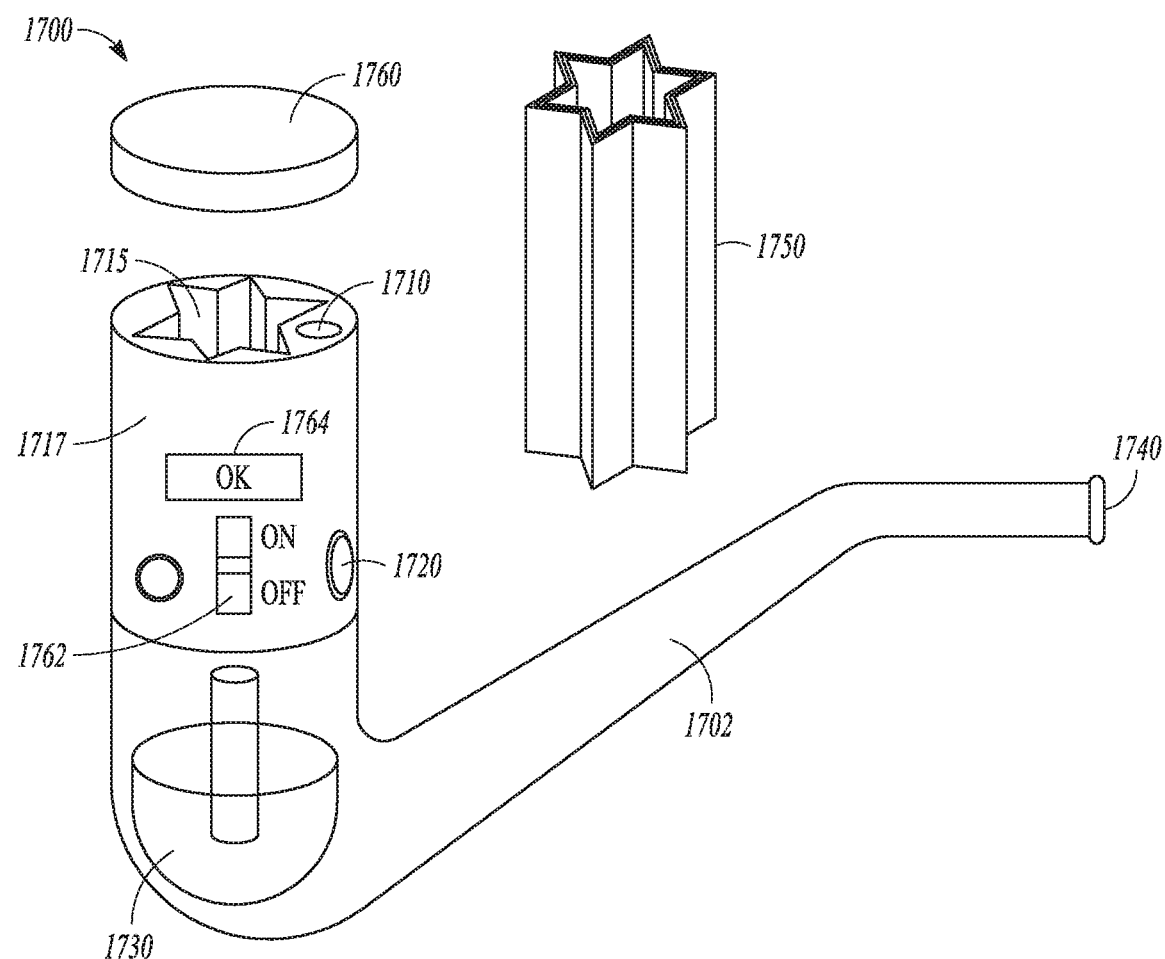
FIG. 17 is a perspective view of an example of a drug delivery system having a drug delivery cartridge in combination with a drug delivery device, in accordance with the present patent application.

FIG. 17 shows a drug delivery system 1700, which can include a drug delivery cartridge 1750 in combination with an example of a drug delivery device, an electronic pipe 1702. The electronic pipe 1702 can include a heating element 1710 with an opening 1715 sized and shaped to receive the drug delivery cartridge 1750, a power unit 1717, an air intake 1720, a moisturizing and cooling chamber 1730, a mouthpiece 1740, a cover 1760, a power switch 1762 and a digital readout 1764.

The heating element 1710 can heat the drug delivery cartridge 1750 to a specified temperature. In an example, the heating element 1710 can pre-heat the drug delivery cartridge 1750 to a temperature less than a volatizing temperature of the drug delivery cartridge 1750 so that the drug delivery cartridge 1750 can readily volatize the coated surface on user demand. In an example, the heating element 1710 can heat the drug delivery cartridge 1750 to a temperature greater than or equal to a volatizing temperature of the one or more drug components to volatize the drug component(s) for delivery of the volatized drug on user demand.

The air intake 1720 provides makeup air to the electronic pipe 1702. In an example, the air intake 1720 can be a hole located in the electronic pipe 1702 in communication with the opening 1715, the moisturizing and cooling chamber 1730 and the mouthpiece 1740. In an example, the air intake 1720 can allow makeup air to flow into the electronic pipe 1702 when a user induces a negative pressure (or suction) action at the mouthpiece 1740.

The cover 1760 can prevent users from contacting the heating element 1710 during operation of the electronic pipe 1702. In an example, the cover 1760 removably attaches to the electronic pipe 1702 to prevent loss of the drug delivery cartridge 1750 during use.

The power switch 1762 controls the flow of electrical power from a power unit 1717 to the heating element 1710. In an example, electrical power can flow from the power unit 1717 to the heating element 1710 when the power switch 1762 is in an 'on' position. In an example, electrical power can be prevented from flowing from the power unit 1717 to the heating element 1710 when the power switch 1762 is in an 'off' position.

The drug delivery cartridge 1750 can be used with the electronic pipe 1702 to deliver a predetermined and accurate quantity of volatized drug to a user. As described above, the amount of the one or more drug components in the cartridge 1750 can be controlled and thus known. The cartridge 1750 can be a single dose cartridge or intended for use over multiple doses. In an example, a user can remove the cover 1760 from the electronic pipe 1702 and insert a drug delivery cartridge 1750 into the opening 1715. In an example, the user can removably attach the cover 1760 to the electronic pipe 1702 before adjusting the power switch 1862 to the 'on' position in order to preheat the drug delivery cartridge 1750. In an example, the user can monitor the digital display 1764 for a visual cue that indicates that the electronic pipe 1702 is ready for use.

A drug delivery device can be configured to control the dosage of the drug to the user such that a multi-dose cartridge can be used with the drug delivery device, while still maintaining dosage control. For example, a drug delivery device similar to the electronic pipe 1702 can be configured to deliver a predetermined amount of drug per inhalation.

The drug delivery device can control how much air passes through the drug delivery cartridge and how much air is delivered to the user. In an example, a valve device inserted into the air flow of the drug delivery device can be used to control the volume of air available to the user. For example, the valve device can be located in the mouthpiece of a drug delivery device to throttle the volume of air flowing through the mouthpiece. In an example, the valve device can include, but is not limited to, a flapper valve, a ball valve, a gate valve, a butterfly valve, a duckbill valve or an adjustable orifice.

In an example, the valve device can include a timer device that can cause the valve device to open or close after an interval of time to regulate air flow through the drug delivery device. For example, the valve device can include an open-loop timer device utilizing mechanisms such as a spring or a mechanical linkage to open or close the valve device. In another example, the valve device can include a closed-loop timer device using an actuator, an electrical control circuit and one or more feedback sensors to implement a control algorithm to open and close the valve.

The drug delivery device can also control other parameters that impact the amount of drug(s) delivered to the user, including, for example, a temperature that the cartridge is heated to and the rate of airflow. Because the drug delivery cartridge only contains the desired components, for example, CBD or THC, which have already been separated from the undesirable components in the source material, sufficient heat can be applied to the drug delivery cartridge to quickly vaporize the drug(s) without worrying about the undesirable components also being vaporized.

The drug delivery cartridge can be configured to control the amount or dose of drug delivered. In an example, the drug delivery cartridge can be coated with a micro porous film to control the flow of drug vapor from the drug delivery cartridge. For example, the diameter of the pores in the micro porous film applied to the coated substrate can be sized to control the dose of drug delivered. In an example, the coated substrate used to form a drug delivery cartridge can be coated with a micro porous film to control the flow of drug vapor from the coated substrate and thereafter formed into a drug delivery cartridge.

In an example, the drug delivery cartridge can be constructed from a coated substrate comprising a conductive material. In an example, the conductive material can include, but is not limited to, aluminum. In an example, an electrical power circuit can be connected to the conductive material to resistively heat the conductive material to a temperature sufficient to volatilize the drug on the coated substrate. In an example, the electrical power circuit can include an electrical control circuit and one or more feedback sensors to resistively heat the conductive material to a sufficient temperature and thereafter accurately maintain the temperature over a period of time.

In an example, the drug delivery cartridges described herein can be used with a vaporizer. The vaporizer can be configured to include a chamber or receptacle that the drug delivery cartridge can be placed in. The drug delivery cartridge can be configured as a single dose or multi-dose cartridge. Given the control parameters that can be used in the process of making the drug delivery cartridge, the drug delivery cartridge can include a known quantity of the drug component(s). As similarly stated above, a heating temperature of the vaporizer is not a significant concern because the drug delivery cartridge only includes the desired components and the substrate used in forming the drug delivery cartridge can be inert at these operating temperatures.

Figure 18:
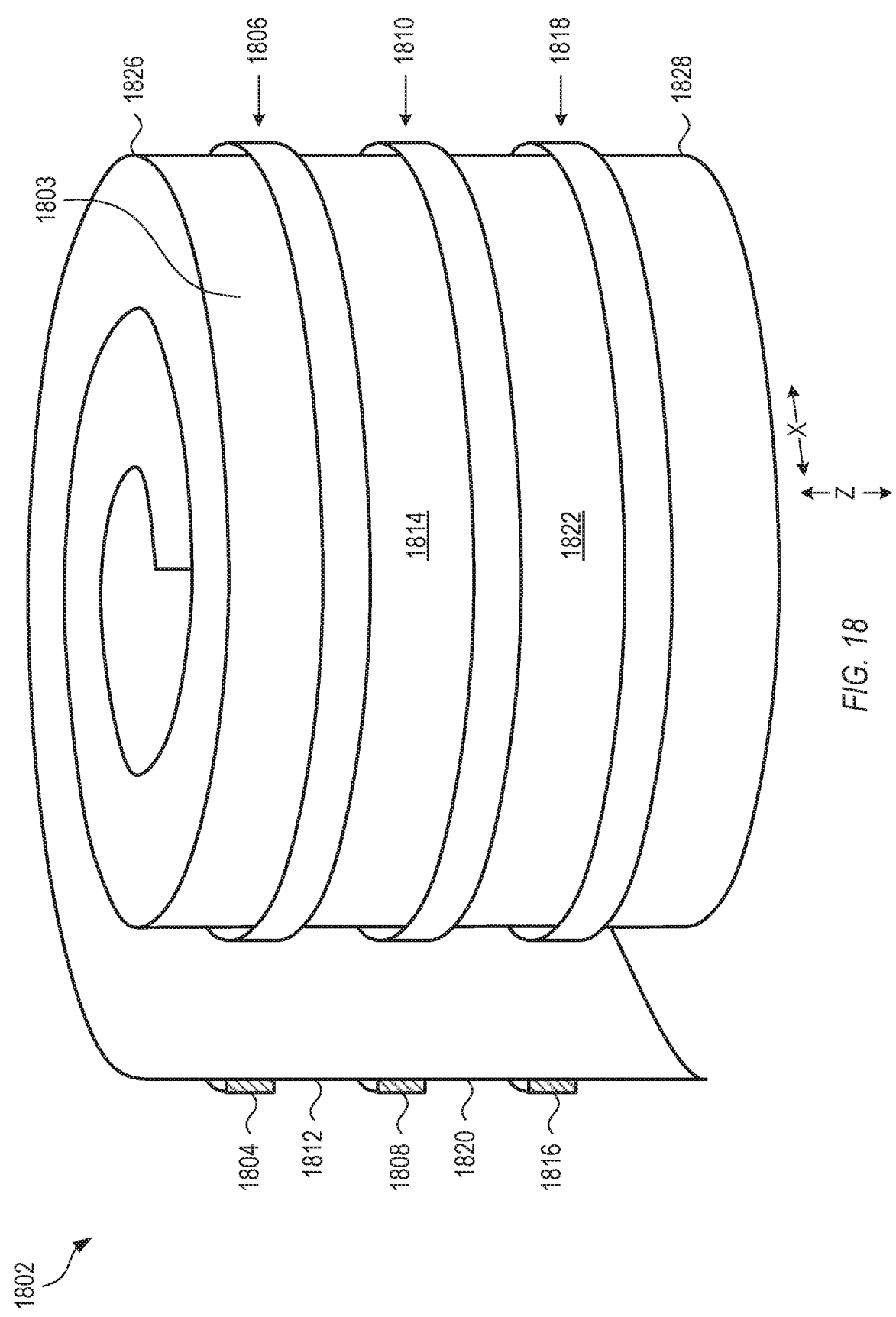
FIG. 18 shows an example of a cylindrically rolled sheet, which can be suitable for use with a drug delivery system.

FIG. 18 shows an example of a cylindrically rolled sheet 1802, which can be suitable for use as a drug delivery cartridge with a drug delivery system. The term cylindrical, as used herein, is intended to mean that the cross-sectional shape of the rolled sheet is the same at each longitudinal location along the rolled sheet 1802. For instance, the cross-section itself can be a circle, a spiral, a curve that lacks sharp corners, a curve that includes at least one sharp corner, a combination of curved and straight portions, a polygon, a square, a star shape, and other suitable shapes. In some examples, the cylindrically rolled sheet can form a tunnel structure that can support air flow therethrough. The rolled sheet 1802 of FIG. 18 is but one example of a cylindrical structure for use as a drug delivery cartridge. As described below, a cylindrical closed-end structure, such as a tube or a star can alternatively be used.

As described above and shown in the figures, any suitable shape can be used for the drug delivery cartridge, and the shape and design is not limited to the examples described and shown herein. As described above, the drug delivery cartridge can be cylindrical such that the cross-sectional shape is the same at each longitudinal location. In other examples, non-cylindrical designs can be used in which the cross-sectional shape varies longitudinally. In other examples, the drug delivery cartridge can be further converted to have a shape configured for use with different drug delivery systems. Further converting can include, for example, shaping a cylindrical structure into a J or an S for use in a pipe.

Referring back to FIG. 18, the rolled sheet 1802 includes a substrate 1803, which can be formed from an electrically conductive material, such as aluminum, copper, or another suitable metal or metal alloy. The rolled sheet 1802 is shaped to allow a gaseous flow in its interior, along the longitudinal direction (Z), from a first longitudinal end 1826 to a second longitudinal end 1828 opposite the first longitudinal end 1826. As further described below, all or a portion of the substrate 1803 can be covered with a coating of a drug component. As described above, in some examples, the drug component can include at least one of THC and CBD. One or both sides of the substrate 1803 can include the drug coating.

The rolled sheet 1802 can include a first electrode 1804 extending laterally (X) across the substrate 1803 at a first longitudinal location 1806. In some examples, the first electrode 1804 can be formed integral to the substrate 1803 to form the rolled sheet 1802, for example, by extruding the electrode 1804 onto the substrate 1803. In those examples, the first electrode 1804 can be thicker relative to the substrate 1803. In some examples, the first electrode 1804 can be originally separate from the substrate 1803 and attached to the substrate 1803, so that the first electrode 1804 is electrically coupled to the substrate 1803 to form the rolled sheet 1802. This is described further below. In some examples, the first electrode 1804 can extend outward from the rolled sheet 1802, toward an exterior of the rolled sheet 1802. In other examples, the first electrode 1804 can extend inward from the rolled sheet 1802, toward an interior of the rolled sheet 1802. In still other examples, the first electrode 1804 can extend both outward and inward from the rolled sheet 1802.

The first electrode 1804 can be formed from an electrically conductive material and can be formed from the same or a different material than the substrate 1803. Example materials include, but are not limited to, aluminum, copper, or another suitable metal or metal alloy. The particular material selected can depend in part on whether the first electrode 1804 is integral to or separate from the substrate 1803. The first electrode 1804 can act a contact portion for use within a housing of a drug delivery system having corresponding electrodes, as described further below.

In an example in which the first electrode 1804 is separate from the substrate 1803, the first electrode 1804 can be made of steel and welded to the substrate 1803 to form the rolled sheet 1802. In such an example, the steel material can optionally be formed or provided as a coiled spring which can be straightened out to weld the material to the substrate and then the material can coil back up as the substrate 1803 is rolled to form the rolled sheet 1802. Other materials and other assembly methods can be used to form the rolled sheet 1802 out of the substrate 1803 and first electrode 1804.

The rolled sheet 1802 can also include a second electrode 1808 extending laterally (X) across the rolled sheet 1802 at a second longitudinal location 1810. The second electrode 1808 can be similar to the first electrode 1804 and have the properties described above. The first and second electrodes 1804, 1808 can each have an electrical resistance small enough to conduct current laterally (X) along the rolled sheet 1802 without heating the rolled sheet 1802. The second electrode 1808 can also be formed as a thick portion of the rolled sheet 1802, or formed separately from the rolled sheet 1802 and attached to the rolled sheet 1802, as described above with reference to the first electrode 1804.

The rolled sheet 1802 can include a first substrate portion 1812 extending longitudinally (Z) between the first and second electrodes 1804, 1808. The first substrate portion 1812 can have an electrical resistance high enough to conduct current longitudinally (Z) between the first and second electrodes 1804, 1808 and resistively heat the first substrate portion 1812 in response to the current conducted therethrough.

A first dose 1814 of a drug can be disposed on the first substrate portion 1812 of the substrate 1803 and configured to volatilize into a gas in response to the resistive heating of the first substrate portion 1812. In some examples, the first dose 1814 of the drug can be uniformly coated on the first substrate portion 1812. In other examples, the first dose 1814 of the drug can include one or more discrete pieces of drug material adhered to the first substrate portion 1812. In some examples, the drug can include THC. In some examples, the drug can include CBD. In some examples, the drug can include a combination of THC and CBD, as described in detail above. In other examples, other suitable drugs can also be used. In some examples, the drug can be coated on an exterior side of the substrate 1803 in the area identified as the first portion 1812. In some examples, the drug can be coated on an interior side of the substrate 1803 in the area identified as the first portion 1812. In some examples, the drug can be coated on both the interior and exterior sides of the substrate 1803. In some examples, different drugs or combinations of drugs can be coated on the interior and exterior sides of the substrate 1803.

In some examples, the rolled sheet 1802 can further include a third electrode 1816 extending laterally (X) across the rolled sheet 1802 at a third longitudinal location 1818, so that the second electrode 1808 is positioned longitudinally between the first and third electrodes 1804, 1816. The third electrode 1816 can have an electrical resistance small enough to conduct current laterally (X) along the rolled sheet 1802 without heating the rolled sheet 1802. The third electrode 1816 can also be formed as a thick portion of the rolled sheet 1802, or formed separately from the rolled sheet 1802 and attached to the rolled sheet 1802.

In some examples, the rolled sheet 1802 can further include a second substrate portion 1820 extending longitudinally (Z) between the second and third electrodes 1808, 1816. The second substrate portion 1820 can have an electrical resistance high enough to conduct current longitudinally (Z) between the second and third electrodes 1808, 1816 and resistively heat the second substrate portion 1820 in response to the current conducted therethrough.

A second dose 1822 of the drug can be disposed on the second substrate portion 1820 and configured to volatilize into a gas in response to the resistive heating of the second substrate portion 1820. In some examples, the first and second doses 1814, 1822 include doses of the same drug. In other examples, the first and second doses 1814, 1822 include doses of different drugs.

In some examples, the rolled sheet can include more than three electrodes, with a corresponding substrate portion between each pair of adjacent electrodes, and a drug dose disposed on each substrate portion of the substrate 1803. As described below in reference to FIGS. 22 and 23, a controller can be used to regulate how and when the drug doses are delivered to an individual.

Figure 19:
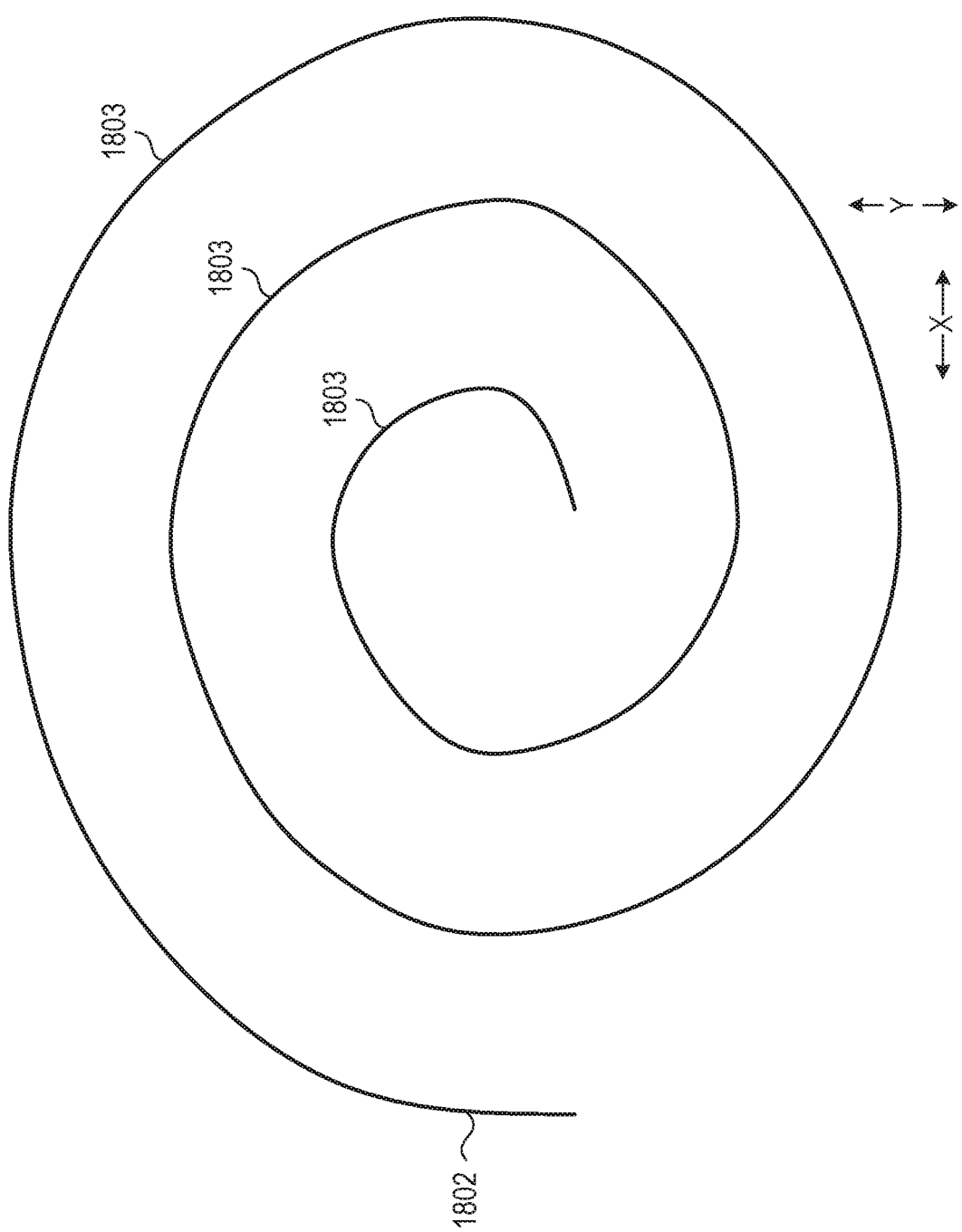
FIG. 19 shows a cross-section of the rolled sheet of FIG. 18.

FIG. 19 shows a cross-section of the rolled sheet 1802 of FIG. 18. In this example, the substrate 1803 is rolled to form a cylindrical structure having a spiral cross-section, when viewed from the first longitudinal end 1826 (FIG. 18) of the rolled sheet 1802. The first, second, and third electrodes are omitted from FIG. 19 for clarity.

Figure 20:
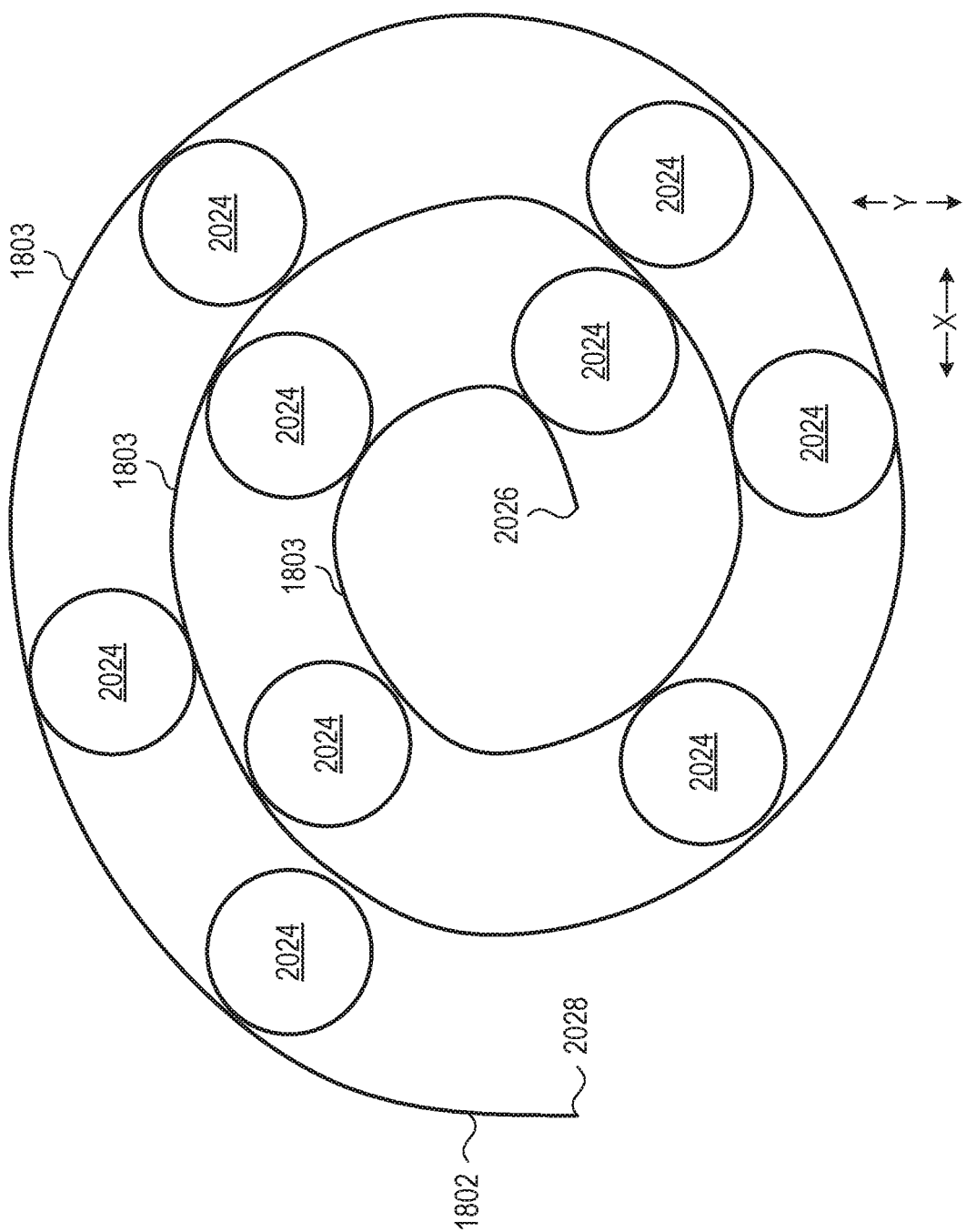
FIG. 20 shows the cross-section of the rolled sheet from FIG. 19, with the addition of an optional plurality of electrically insulating spacers positioned to space apart adjacent rolls of the rolled sheet.

FIG. 20 shows the cross-section of the rolled sheet 1802 from FIG. 19, with the addition of an optional plurality of electrically insulating spacers 2024 positioned to space apart adjacent layers of the substrate 1803. The spacers 2024 can be similar to the spacers described above in reference to FIGS. 7A and 7B. The electrically insulating spacers 2024 can be positioned and spaced apart to allow a gaseous flow in the interior of the rolled sheet 1802, along the longitudinal direction, from the first longitudinal end 1826 (FIG. 18) to the second longitudinal end 1828 (FIG. 18). The spacers 2024 can be added to the substrate 1803 prior to forming the rolled sheet 1802 or after the rolled sheet 1802 is assembled.

In the examples of FIGS. 18-20, the substrate 1803 is rolled in an open-ended manner to form the rolled sheet 1802, so that one of its lateral edges 2026 is disposed at the center of the rolled sheet 1802 and the opposite lateral edge 2028 is disposed at the exterior of the rolled sheet 1802. In other examples, the substrate 1803 can be assembled in a closed-ended manner, so that for some methods of assembly, its lateral edges can be joined during assembly to form a tube or other cylindrical structure.

Figure 21:
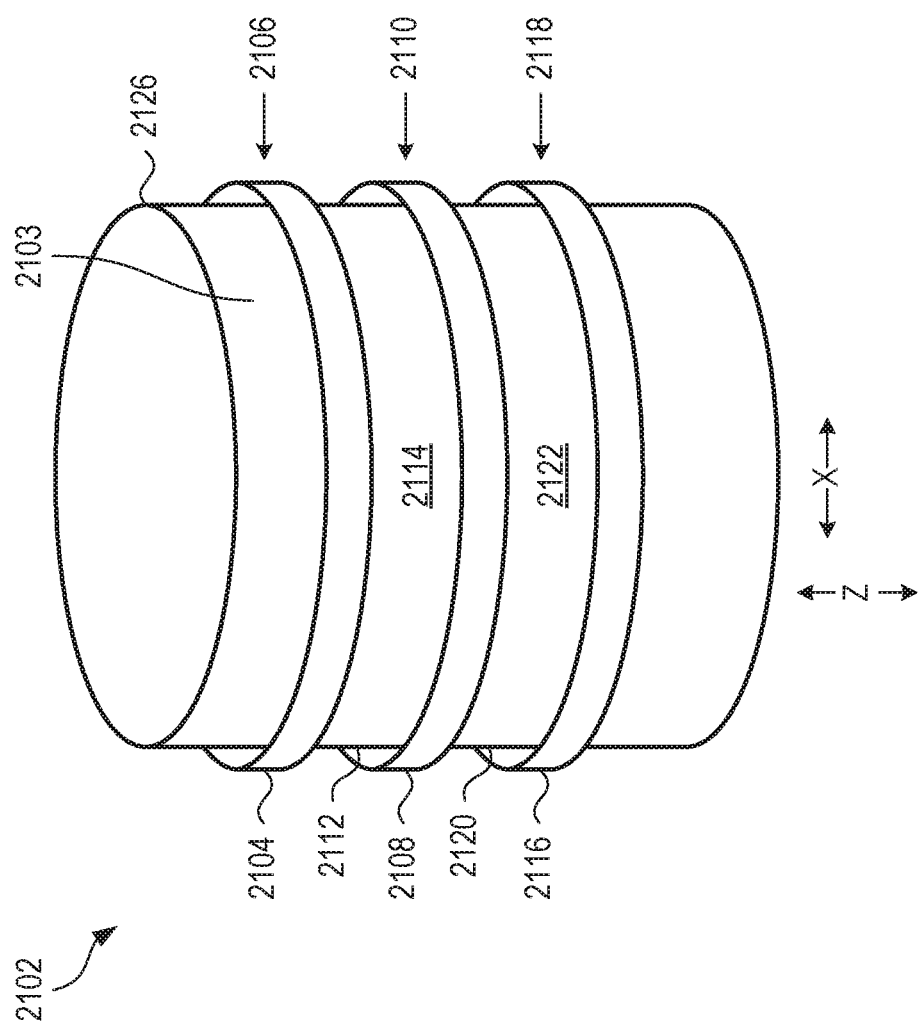
FIG. 21 shows another example of a cylindrically rolled sheet.

FIG. 21 shows an example of a tube 2102, suitable for use as a drug delivery cartridge in a drug delivery system. In the example of FIG. 21, the tube 2102 has a circular cross-section, when viewed from a longitudinal end 2126 of the tube 2102. The tube 2102 is formed of a substrate 2103, and as described above, all or a portion of the substrate 2103 can be coated with one or more drugs. The tube 2102 includes a first electrode 2104 at a first longitudinal location 2106, a second electrode 2108 at a second longitudinal location 2110, a first substrate portion 2112 extending longitudinally (Z) between the first and second electrodes 2104, 2108, a first dose 2114 of a drug disposed on the first substrate portion 2112, a third electrode 2116 disposed at a third longitudinal location 2118, a second substrate portion 2120 extending longitudinally (Z) between the second and third electrodes 2108, 2116, and a second dose 2122 of a drug disposed on the second substrate portion 2120. In some examples, only one side of the substrate 2103 is coated with the one or more drugs such that the drug doses are disposed on the exterior of the tube 2102 or the interior of the tube 2102. In some examples, both sides of the substrate 2103 are coated with the one or more drugs such that the drug doses are disposed on the interior and exterior of the tube 2102.

In an example in which the cylindrical structure is a tube, like the tube 2102, the tube 2102 can be formed in at least the two ways described herein. Other processes can alternatively or additionally be used to form the cylindrical structure. In a first process, the first electrode 2104 can be open and have a lateral dimension generally equal to a lateral dimension of the substrate 2103. The first electrode 2104 can include a hinge, which can be generally located at a lateral mid-point on the first electrode 2104. It is recognized that the hinge can be at other lateral locations on the first electrode 2104, and more than one hinge can be used. The first electrode 404 and the substrate 2103 can be brought together such that the first and second lateral ends of each of the substrate 2103 and the electrode 2104 are generally aligned. The first and second lateral ends of the substrate 2103 and the electrode 2104 can then be connected together to form a closed, tubular structure, with the electrode 2104 connected to an exterior circumference of the substrate 2103. Additional electrodes can similarly be attached to the substrate 2103 to form a tube having multiple electrodes at various longitudinal locations on the substrate 2103.

In a second process, the first electrode 2104 can be a closed-end structure, having a generally circular shape; the substrate 2103 can be converted into a tube by joining the first and second longitudinal ends of the substrate 2103. The converted substrate 2103 can then be inserted into the circular electrode 2104 such that the electrode 2104 is connected to an exterior circumference of the substrate 2103. If the tube 2102 is intended to have multiple electrodes, the converted substrate 2103 can be separately inserted into each electrode, or the multiple electrodes can be longitudinally spaced from one another and the converted substrate 2103 can be inserted into the multiple electrodes in one step. In some examples, a support structure can be used to support the one or more electrodes as the converted substrate 2103 is inserted into the one or more electrodes.

One of ordinary skill in the art will appreciate that the drug delivery cartridge can have any suitable cross-section, such as spiral (FIGS. 17-20), circular (FIG. 21), elliptical, rounded and elongated, square, star-shaped, regular and irregular polygonal, and so forth.

Figure 22:
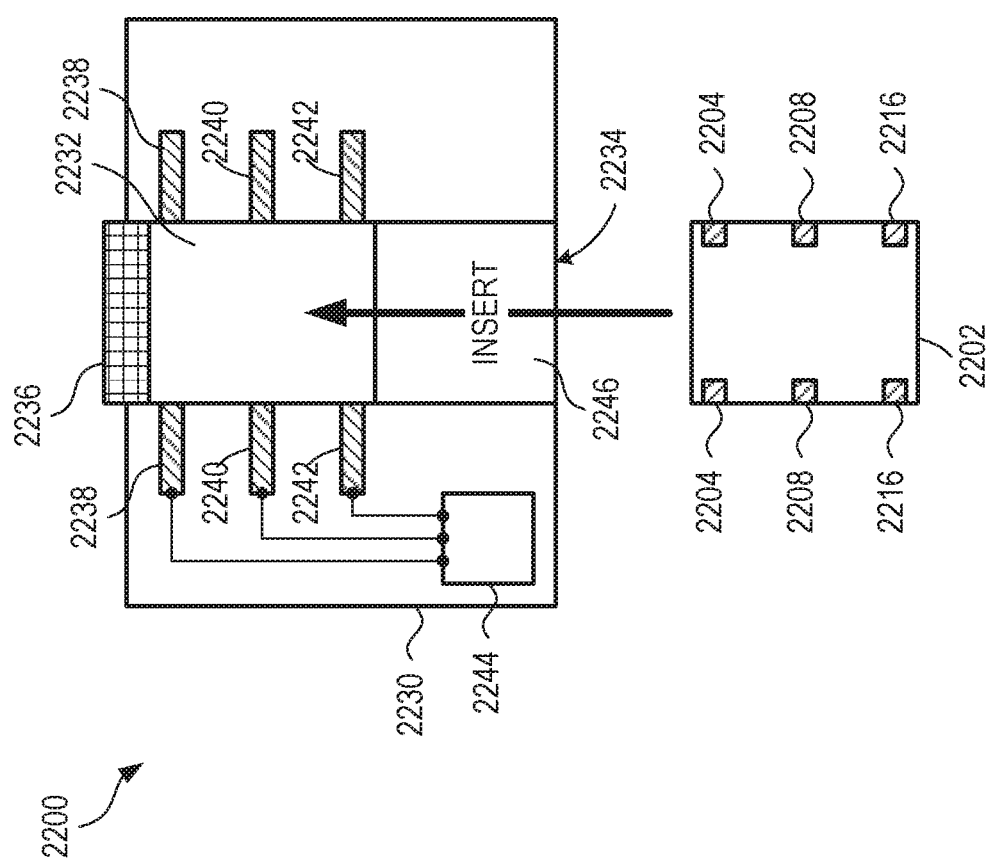
FIGS. 22 and 23 show an example of a drug delivery system.
Figure 23:
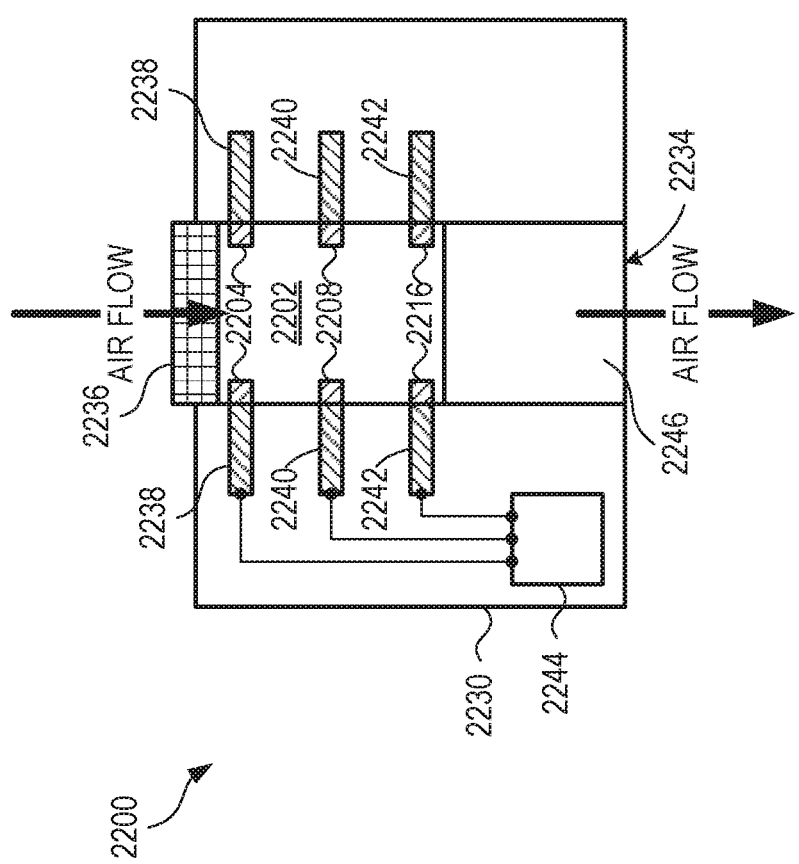

FIGS. 22 and 23 show an example of a drug delivery system 2200. The drug delivery system 2200 can include a drug delivery cartridge 2202, which can be similar to the rolled sheet 1802 (FIGS. 17-20) or alternatively can be a tube such as the tube 2102 (FIG. 21). The drug delivery system 2200 can further include a housing 2230. FIG. 5 shows the rolled sheet 2202 separate from the housing 2230, which is how the drug delivery system 2200 can be arranged as sold or during storage. FIG. 23 shows the rolled sheet 2202 inserted into the housing 2230, which is how the drug delivery system 2200 can be arranged during use.

In some examples, the housing 2230 can be configured to be reusable, and the rolled sheet 2202 can be configured to be disposable or recyclable after the drug dosages have been delivered. In some of these examples, the rolled sheet 2202 can be packaged as a replaceable cartridge. In other examples, the housing 2230 and rolled sheet 2202 can be packaged together, with one or both being configured to be disposable or recyclable after the drug dosages have been delivered. In some examples, the housing 2230 can be elongated and can include a first longitudinal end configured to deliver the volatilized gas into a user's mouth.

The housing 2230 can be configured to receive the rolled sheet 2202 within a cylindrical cavity 2232. The cylindrical cavity 2232 can be accessed through an opening 2234 in the housing 2230. In some examples, such as the example of FIG. 22, the opening 2234 can face a user, during use. In some of these examples, the opening 2234 is configured to deliver the volatilized gas into a user's mouth. For these examples, the housing 2230 can include an air filter 2236, attached to or made integral with the housing 2230, positioned on an opposite side of the cylindrical cavity 2232 as the opening 2234, and configured to filter air intake as air flows from outside the housing 2230, through air filter 2236, toward the cylindrical cavity 2232. In other examples, the opening 2234 can face away from a user, during use. In these examples, the rolled sheet 2202 can optionally include an air filter. In some examples, the cylindrical cavity 2232 and the rolled sheet 2202 can be keyed, or can include one or more locating features that can ensure that the rolled sheet 2202 is inserted into the cylindrical cavity 2232 with a specified rotational orientation. The housing 2230 can be designed to receive drug delivery cartridges having alternative shapes to the cylindrical design of the drug delivery cartridge 2200 by having the cavity 2232 in the housing 530 be sized and shaped to correspond to the size and shape of the drug delivery cartridge.

The housing 2230 can include a first housing electrode 2238 around a circumference of the cylindrical cavity 2232 and facing inward toward the cylindrical cavity 2232. The first housing electrode 2238 can be positioned longitudinally to respectively contact the first electrode 2204 of the rolled sheet 2202 when the rolled sheet 2202 is inserted into the housing 2230. The first housing electrode 2238, as well as additional housing electrodes, can be formed from stainless steel, aluminum, copper, or other suitable conductive materials.

The housing 2230 can include a second housing electrode 2240 around a circumference of the cylindrical cavity 2232 and facing inward toward the cylindrical cavity 2232. The second housing electrode 2240 can be positioned longitudinally to respectively contact the second electrode 2208 of the rolled sheet 2202 when the rolled sheet 2202 is inserted into the housing 2230. The first and second housing electrodes 2238, 2240 can be configured to deliver current between the first and second electrodes 2204, 2208 of the rolled sheet 2202. The first and second housing electrodes 2238, 2240 can be part of a heating element to deliver current between the first and second electrodes 2204, 2208 of the rolled sheet 2202 such that a portion of the rolled sheet 2202 can be resistively heated, as an alternative to using heated air.

The housing 2230 can optionally include a third housing electrode 2242 around a circumference of the cylindrical cavity 2232 and facing inward toward the cylindrical cavity 2232. The third housing electrode 2242 can be positioned longitudinally to respectively contact the third electrode 2216 of the rolled sheet 2202 when the rolled sheet 2202 is inserted into the housing 2230. The second and third housing electrodes 2240, 2242 can be configured to deliver current between the second and third electrodes 2208, 2216 of the rolled sheet 2202.

In some examples, the rolled sheet 2202 and housing 2230 can include more than three electrodes and housing electrodes, respectively. For these examples, each pair of adjacent housing electrodes can be configured to deliver current between a corresponding pair of adjacent electrodes of the rolled sheet.

In some examples, a controller 2244 can be positioned in the housing 2230. The controller 2244 can be configured to deliver current to the housing electrodes 2238, 2240 and 2242. In some examples, the controller can deliver current between the first and second housing electrodes 2238, 2240 at a first time to provide a first dose of a drug to a user. In some examples, the controller 2244 can be further configured to deliver current between the second and third housing electrodes 2240, 2242 at a second time, different from the first time, to provide a second dose of the drug to the user. For drug delivery cartridges that include multiple doses, the controller 2244 can be configured to deliver current between adjacent pairs of housing electrodes at sequential times to provide a dose of the drug to a user at each sequential time. In some examples, the controller 2244 can deliver current to multiple pairs of housing electrodes at the same time to deliver multiple doses to the user with a single inhalation. By using a conductive substrate and delivering current to the electrodes, the drug can be volatilized and inhaled by the user using room temperature air instead of heated air.

In some examples, the controller 2244 can include one or more batteries. In some examples, the controller 2244 can be rechargeable. In some examples, the controller 2244 can communicate with other electronic devices, such as through short-range wireless communication. In some examples, the controller 2244 can communicate with the Internet. In some of these examples, the controller 2244 can record a user's dosage history through wireless communication with another electronic device or through a web-based application. The controller 2244 can be triggered through a button on the housing 2230, through a touch-sensitive area on the housing configured to activate the controller 2244 when the 2230 housing contacts a user's mouth, or through another suitable trigger.

During use, as a user inhales, such as through opening 2234, the user can draw in air from the surroundings through the air filter 2236. The air from the surroundings can combine with the dose of the drug released from the rolled sheet 2202 in an optional expansion/mixing chamber 2246.

In some examples, the expansion/mixing chamber 2246 can be positioned between the rolled sheet 2202 and the user's mouth, during use.

After use, once the doses of the drug on the rolled sheet 2202 have been dispensed, the housing 2230 can eject or release the expended rolled sheet 2202. The expended rolled sheet 2202 can then be thrown away or recycled. In some examples, the housing 2230 can optionally include storage for one or more additional rolled sheets 2202.

Figure 24:
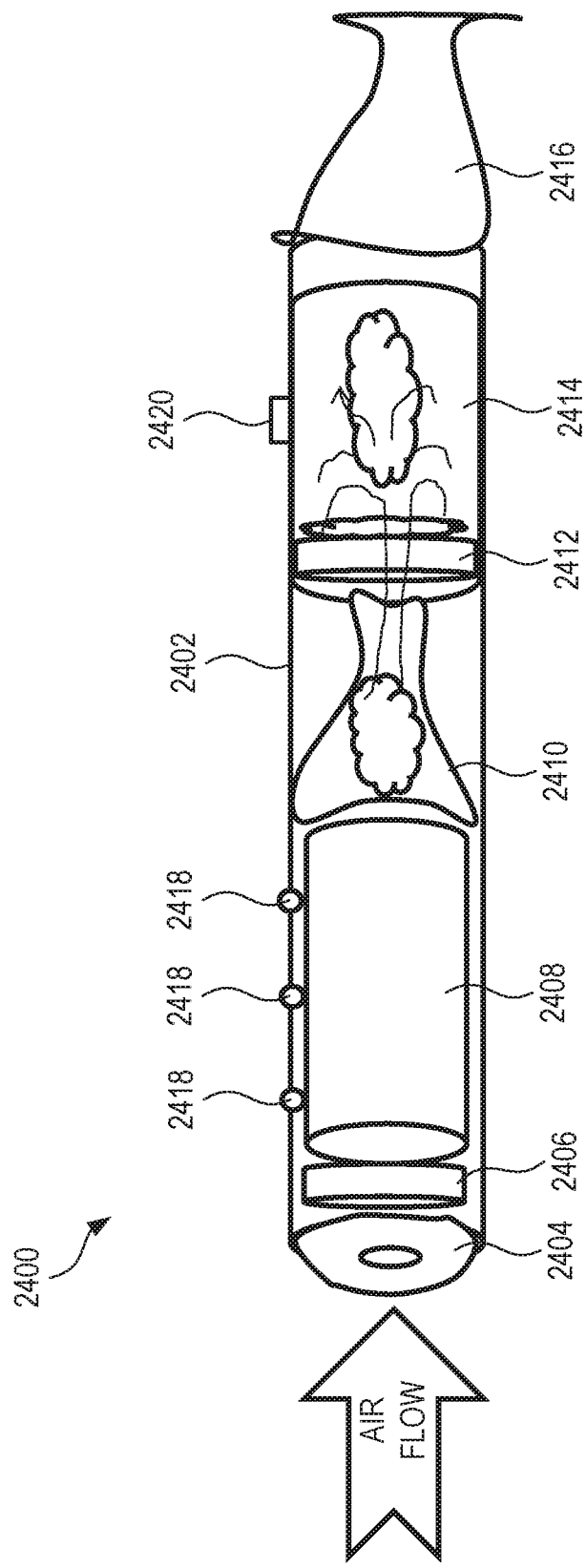
FIG. 24 is a side-view schematic drawing of another example of a drug delivery system.

FIG. 24 is a side-view schematic drawing of another example of a drug delivery system 2400. The example of FIG. 24 is sized and shaped for ease of use by a user. The drug delivery system 2400 can include a housing 2402.

An air intake nozzle 2404 can receive air flow from the surroundings and can optionally restrict the air flow into the housing 2402. In some examples, the air intake nozzle 2404 can be adjustable. In some examples, the air intake nozzle 2404 can allow a user to control the rate at which the surrounding air is taken into the housing 2402. In some examples, the air intake nozzle 2404 can control a duration of an inhalation. In some examples, the air intake nozzle 2404 can produce an internal pipe pressure when the user inhales.

Air passing through the air intake nozzle 2404 can pass through an air filter 2406. The air filter 2406 can prevent particles or particulate from entering further into the housing 2400. In some examples, the air filter 2406 can be the same in structure and function as the air filter 2236 (FIGS. 22 and 23).

Air passing through the air filter 2406 can enter a volatilizing chamber 2408. In some examples, the volatilizing chamber 2408 can accommodate one or more drug delivery cartridges, such as 1802 (FIGS. 17 and 18), 2102 (FIG. 21), or 2202 (FIGS. 22 and 23). An interior of the volatilizing chamber 2408 can include electrodes that connect to corresponding electrodes on a rolled sheet during use. Air leaving the volatilizing chamber 2408 can include a prescribed dose of the drug, which is volatilized from the cartridge during use.

A vortex chamber 2410 can reduce a cross-section surface area of gas passing therethrough. The reduced surface area can increase the velocity of gas passing therethrough, which can be desirable.

Gas leaving the vortex chamber 2410 can pass through a misting ring 2412, which can optionally inject mist from a misting reservoir 2422 into the gas. In some examples, the mist can include water. In some examples, the mist can include one or more flavorings or scents. In some examples, the misting ring 2412 can be activated by a controller, such as 2244 (FIGS. 22 and 23). In some examples, the misting reservoir 2422 is refillable. In some of these examples, the housing 2402 can define a port 2424, through which the misting reservoir 2422 can be refilled. In some of these examples, the material to refill the misting reservoir 2422 can be poured through the port 2424 in the housing 2402. In some examples, the material to refill the misting reservoir 2422 can be inserted via a cartridge, or other container, through the port 2424 in the housing 2402. As described further below in reference to FIG. 25, a pump can be used with the reservoir 2422 to deliver the solution from the reservoir 2422 to the misting ring 2412. As shown in FIG. 24, in an example, the misting reservoir 2422 can be located within the vortex chamber 2410. In other examples, the misting reservoir 2422 can be located in an alternative location within the housing 2402 or external to the housing 2402.

Gas leaving the misting ring 2412 can enter a mixing chamber 2414. The gas, moving with an increased velocity from the vortex chamber 2410, can expand within the mixing chamber 2414. This expansion can form a vortex, which can improve mixing of the mist with the gas. The inclusion of a misting ring in the drug delivery system 2400 can be used to moisturize and cool the air leaving the volatilizing chamber 2408 and can improve inhalation of the vapors from the drug delivery cartridge. The mist can be added to the vapors using additional or alternative features to the misting ring 2412. In an example, a misting solution can be packaged separately or together with a drug delivery cartridge. The misting solution can be available in different flavors to accommodate user preferences. It is recognized that the misting ring 2412 or comparable misting feature can be used in the other drug delivery systems described above. The misting ring 2412 can be used independently of the housing electrode design of FIG. 24. The drug delivery system 2400 of FIG. 24 can alternatively exclude the misting ring 2412.

Gas from the mixing chamber 2414 can exit the housing 2402 through a mouthpiece 2416. In some examples, the mouthpiece 2416 is removable from the housing 2402. A removable mouthpiece 2416 can help ensure sterility for the user. In other examples, the mouthpiece 2416 can be attached to and non-removable from the housing 2402.

The housing 2402 can include an optional status indicator, which can display visual indicia that indicate a status of the housing during use. In the example of FIG. 24, the status indicator can include three light emitting diodes (LEDs) radiating outward from the housing 2402. This is but one example of a status indicator; other suitable examples can also be used.

In the specific example of FIG. 24, each LED 2418 corresponds to a housing electrode and a corresponding electrode on the rolled sheet. In the specific example of FIG. 24, when the cartridge is inserted into the volatilizing chamber 2408, the controller can sense a voltage drop across adjacent pairs of electrodes, and can direct corresponding LEDs 2418 to glow red. In this example, a red color indicates that a corresponding dose on the rolled sheet is ready to be volatilized. In this example, a user can depress a button 2420 on the housing 2402, which can instruct the housing to direct current through a corresponding portion of the substrate. The button 2420 can operate as a 'go button'. In other examples, the button 2420 can include additional functionality with regards to operating the drug delivery system 2400. In the specific example of FIG. 24, when the user depressed the button for the first time, for a particular rolled sheet, corresponding LEDs can alternately blink red and green. In a specific example, blinking red and green can indicate that the controller is heating a selected dose on the rolled sheet. In some examples, the heating can take a relatively short period of time, such as two seconds. In some examples, when a dose is ready to be volatilized, a corresponding LED can turn solid green. In some examples, when a user depresses the button 2420 for a second time, the controller can monitor an internal pressure, such as in the volatilizing chamber 2408 or the mixing chamber 2414. In some examples, the controller can include a pressure sensor that detects a drop in pressure. When the pressure drops, corresponding to an inhalation by the user, the controller can volatilize the corresponding drug dose on the rolled sheet. In some examples, the pressure sensor can provide a rate at which the drug is being depleted to the controller. In some examples, one or more LEDs can blink at a rate indicative of the rate at which the drug is depleted. In some examples, when the controller determines that a dose of the drug is fully dispensed, one of more LEDs can turn off.

In other examples, more or less than the three LEDs 2418 can be used in the housing 2402. The LEDs as described above are but one specific example of a status indicator; other status indicators can also be used.

As shown in FIG. 24, the drug delivery system 2400 can optionally include a dose selection switch 2426 for selecting how many dosages are dispensed at one time from a drug delivery cartridge inserted in the chamber 2408. In some examples, the dose selection switch 2426 can include settings labeled as "1", "2", "3", . . . , up to the number of doses capable of being delivered from the cartridge. For example, if the dose selection switch 2426 is set to "3", then the drug delivery system 2400 can dispense three doses from the cartridge at one time.

Figure 25:
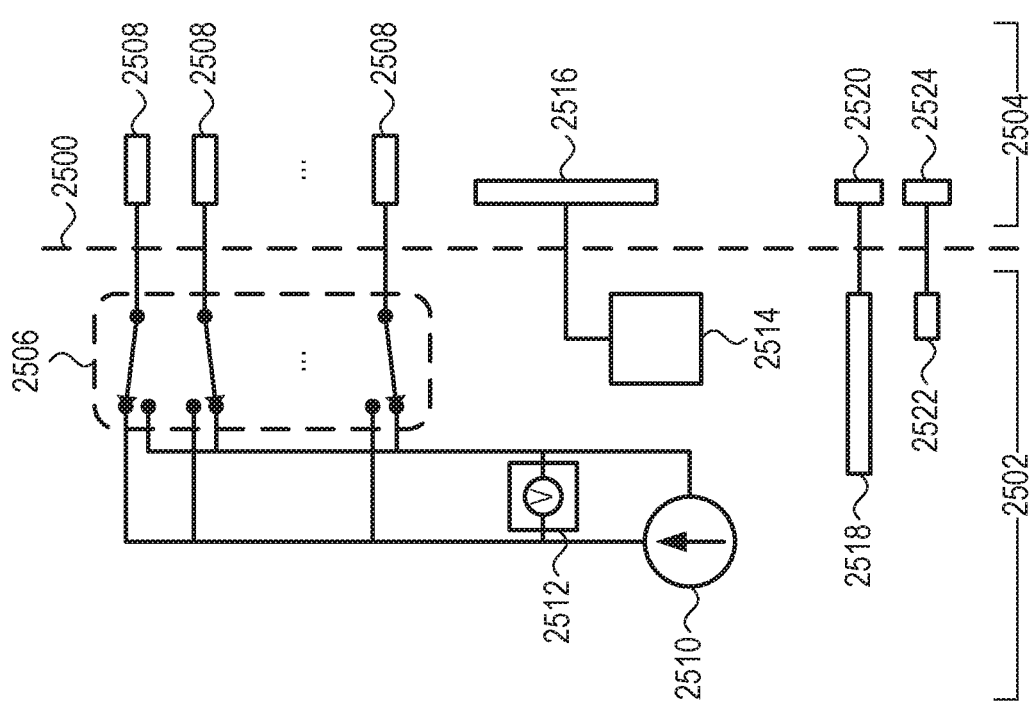
FIG. 25 is a schematic drawing of an example of an interface connector for use with a vaporizer pipe and controller.

FIG. 25 is a schematic drawing of an example of an interface connector 2500. The interface connector 2500 can form various connections, including electrical, hydraulic, and gaseous connections, between a controller 2502 for a vaporizing pipe for a drug delivery system, such as 2400 (FIG. 24), and the vaporizing pipe 2504 itself. The interface connector 2500 is but one example of a connector; other suitable connectors can also be used. The vaporizing pipe 2504 is similar to the pipe shown in FIG. 24. The controller 2502 can be external to the pipe 2504, attachable thereto, or integrally formed therewith. The interface connector 2500, the controller 2502 and the vaporizing pipe 2504 can be part of the drug delivery system.

A controllable switching matrix 2506 can control voltages directed to each electrode 2508 on a drug delivery cartridge usable in the vaporizing pipe 2504. The controller 2502 can include a controllable current source 2510 to generate the current, and a voltage detector 2512 to monitor the voltage across the leads of the current source 2510. The controllable switching matrix 2506 can controllably switch the electrical connection of each electrode between the two sides of the current source 2510, thus switching or alternating a voltage applied to each electrode between a relatively low value and a relatively high value. When the relative voltages between a pair of adjacent electrodes 2508 are equal (e.g., both relatively low or both relatively high), then no current flows between the electrodes 2508. When the voltages between the pair of adjacent electrodes 2508 are different (e.g., one relatively low and one relatively high), then current flows from the electrode having the relatively high voltage to the electrode having the relatively low voltage. The current generates heat, and the heat volatilizes the desired dose of the drug, which is disposed between the electrodes 2508 in the pair, as described above. The controller 2502 can track which doses have been volatilized, so that current is directed through each adjacent pair of electrodes 2508 only a single time during use of a particular drug delivery cartridge.

As shown in FIG. 25, a misting reservoir and pump 2514 can be included in the same mechanical housing as the controllable switching matrix 2506 and, in an example, can be housed within the controller 2502. The interface connector 2500 can hydraulically connect the controller 2502 to the vaporizing pipe 2504 such that the misting reservoir and pump 2514 can controllably direct a specified volume of mist, through the interface connector 2500, to a mister 2516, such as a misting ring 2412 (FIG. 24). In some examples, the controller 2502 supplies a fixed volume of mist for each dose of the drug. In some examples, the controller 2502 allows a user to select the volume of mist for each dose of the drug. For instance, the mist volume can be selected mechanically, such as with a knob, level, or button on the housing.

Alternatively, the mist volume can be selected electronically, such as by one or more buttons on the housing of the vaporizing pipe 2504 or the controller 2502.

A pressure sensor 2518 can be included in the controller 2502. The pressure sensor 2518 can measure one or more pressures in the drug delivery system 2504, such as at an orifice 2520, which can be located, for example, proximate to the mouth of the user. In some examples, the controller 2502 can use the pressure sensor 2518 as a trigger switch, which can trigger additional actions from the controller 2502. When the user inhales from the vaporizing pipe 2504, the pressure at a particular location, such as at the orifice 2520, drops. The pressure sensor 2518 can detect the drop in pressure, and the controller 2502 can take a suitable action, such as directing suitable voltages to the electrodes 2508 to initiate delivery of a drug dose, and/or directing the misting reservoir 2514 to dispense mist. In other examples, the controller 2502 can connect to a Get Ready/Go button on the housing, similar to the button 2420 shown in FIG. 24, to trigger suitable actions.

The interface connector 2500 can optionally include additional electrical connections between the controller 2502 and the vaporizing pipe 2504. For instance, an optional LED controller 2522 can electrically connect, through the interface connector 2500, to one or more LEDs 2524 on or in the housing. In some examples, the controller 2502 can additionally connect to a dose selection switch disposed on the housing. In some examples, the controller can electrically connect to a power source disposed on or in the housing.

Although several features, for example, the misting reservoir and pump 2514, are described above as being part of the controller 2502, it is recognized that some or all of these features do not have to be physically contained within the same housing as the controller 2502 but can still be controlled by the controller 2502.

It is recognized that a drug delivery system, like the system 2400 of FIG. 24, can exclude a controller, or a controller could be used having more or less features as the controller 2502 shown in FIG. 25. In a drug delivery system that excludes a controller, a user can manually control operation of the electrodes (or other means of volatilizing the drug), or similarly, the user can manually deliver a misting solution to a mixing chamber by manually activating the pump for the mist reservoir.

There can be potential advantages to delivering the drug using the drug delivery cartridges described herein. For instance, the drug dosage and purity can be accurately controlled during the manufacturing process. In some examples, an advantage can include allowing a user to ingest THC and CBD in a safe, repeatable accurate dose suitable for research and clinical trials. In some examples, an advantage can include forming the cartridge from recyclable aluminum. In some examples, an advantage can include depositing the THC/CBD drugs onto the aluminum substrate in a carefully controlled and regulated process, transported to the user. In some examples, an advantage can include removing the toxins during factory processing and disposing of the toxins properly. In some examples, an advantage can include recycling the cartridge, with no waste. In some examples, an advantage can include convenience for the user, and lack of smoke when used. In some examples, an advantage can include disposing multiple doses on a single cartridge, which further enhances convenience, functionality as well as lowering shipping cost. In some examples, an advantage can include the flexibility in accurately setting a dose level, which can provide functionality to both users and researchers alike. In some examples, an advantage can include optionally adding a moisturizing mist, and perhaps a pleasant flavor, which improves the overall experience and comfort for the user.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples and the embodiments described below (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The present application provides for the following exemplary embodiments, the numbering of which is not to be construed as designating levels of importance:

Embodiment 1 provides a method of purifying at least one of THC and CBD from a *cannabis*-containing composition and the method can comprise heating the *cannabis*-containing composition to a first temperature to volatilize at least one of THC and CBD into a first vapor, and condensing the first vapor onto a substrate to form a first coating, the first coating comprising at least one of THC and CBD.

Embodiment 2 provides the method of Embodiment 1 optionally configured such that the first coating comprises THC and the method optionally further comprising, after forming the first coating, heating the *cannabis*-containing composition to a second temperature to volatilize CBD into a second vapor, and condensing the second vapor onto the substrate to form a second coating over the first coating, the second coating comprising CBD. The second temperature is greater than the first temperature.

Embodiment 3 provides the method of Embodiment 1 optionally configured such that the substrate includes a first side and a second side and the first coating is formed on the first side of the substrate and comprises THC. The method optionally further comprises heating the *cannabis*-containing composition to a second temperature to volatilize CBD into a second vapor, the second temperature greater than the first temperature, and condensing the second vapor onto the second side of the substrate to form a second coating, the second coating comprising CBD.

Embodiment 4 provides the method of Embodiment 1 optionally configured such that the first coating comprises THC and the method optionally further comprising, after forming the first coating, heating the *cannabis*-containing composition to a second temperature to volatilize CBD into a second vapor, the second temperature greater than the first temperature, and condensing the second vapor onto a second substrate to form a coating comprising CBD.

Embodiment 5 provides the method of Embodiment 1 optionally configured such that the first temperature is equal to or greater than a temperature sufficient to volatilize CBD, and the first coating comprises THC and CBD.

Embodiment 6 provides the method of any of Embodiments 1-5 optionally configured such that condensing the first vapor onto a substrate includes placing the substrate on or near a cooling bar.

Embodiment 7 provides the method of any of Embodiments 1-6 optionally configured such that the *cannabis*-containing composition is raw *cannabis*.

Embodiment 8 provides the method of Embodiment 7 optionally further comprising processing the raw *cannabis* into smaller pieces prior to heating the raw *cannabis*.

Embodiment 9 provides a method of concentrating at least one of THC and CBD from a *cannabis*-containing composition and the method can comprise (a) heating the *cannabis*-containing composition to a first temperature to volatilize at least one of THC and CBD into a first vapor, (b) condensing the first vapor onto a substrate to form a first coating comprising at least one of THC and CBD, and (c) processing the substrate into substrate pieces thereby increasing a total surface area of the processed substrate. The method can further comprise (d) heating the substrate pieces to the first temperature to volatize at least one of THC and CBD into a second vapor, and (e) condensing the second vapor onto a second substrate to form a second coating comprising at least one of THC and CBD. A weight fraction of the at least one of THC and CBD in the second coating can be greater than the weight fraction of the at least one of THC and CBD in the first coating.

Embodiment 10 provides the method of Embodiment 9 optionally further comprising repeating steps (c)-(e) until the weight fraction of the at least one of THC and CBD in the subsequent coating exceeds a specified level.

Embodiment 11 provides a method of making a drug delivery cartridge and can comprise heating a *cannabis*-containing composition to a first temperature to volatize at least one of THC and CBD into a first vapor, condensing the first vapor onto a substrate to form a coating on the substrate comprising at least one of THC and CBD, and converting the coated substrate into a three-dimensional structure configured for use as a drug delivery cartridge.

Embodiment 12 provides the method of Embodiment 11 optionally configured such that converting the coated substrate includes rolling the coating substrate to form a spirally-wound cylindrical shape.

Embodiment 13 provides the method of Embodiment 12 optionally configured such that a plurality of spacers is placed along the coated substrate prior to converting. The plurality of spacers can be configured to allow for airflow through the spirally-wound cylindrical shape.

Embodiment 14 provides the method of Embodiment 11 optionally configured such that the coated substrate comprises a first end and a second end opposite to the first end and the method can further comprise creating a plurality of notches at multiple locations on the coated substrate between the first and second ends. The notches can create an interface and an interval between adjacent notches defines a segment of coated substrate. The method can further comprise bending the segments relative to one another at the interfaces so as to form a saw-tooth pattern.

Embodiment 15 provides the method of Embodiment 14 optionally further comprising connecting the first end to the second end to form a closed polygonal shape.

Embodiment 16 provides the method of any of Embodiments 11-15 optionally further comprising ascertaining an average amount of at least one of THC and CBD in the coating per unit area of the coated substrate.

Embodiment 17 provides the method of any of Embodiments 11-16 optionally configured such that converting the coated substrate into a three-dimensional structure includes determining a total area of the coated substrate to use for the three-dimensional structure based on a predetermined amount of the at least one of THC and CBD in the drug delivery cartridge.

Embodiment 18 provides the method of any of Embodiments 11-17 optionally further comprising attaching one or more layers to the coated substrate prior to converting the coated substrate into a three-dimensional structure, the one or more layers configured to provide at least one of flavor or enhancement of the at least one of THC and CBD.

Embodiment 19 provides the method of any of Embodiments 11-18 optionally further comprising heating the *cannabis*-containing composition to a second temperature greater than the first temperature to volatilize CBD into a second vapor prior to converting the coated substrate into a three-dimensional structure, and condensing the second vapor onto the substrate to form a second coating on the substrate, the second coating comprising CBD.

Embodiment 20 provides the method of any of Embodiments 11-19 optionally configured such that the first temperature is equal to or greater than a temperature sufficient to volatilize CBD and the first coating comprises THC and CBD.

Embodiment 21 provides a drug delivery product comprising a coated substrate with one or more coating layers, the one or more coating layers including at least one of THC and CBD.

Embodiment 22 provides the drug delivery product of Embodiment 21 optionally configured such that the coated substrate is converted into a three-dimensional structure configured to maximize surface area of the three-dimensional structure and allow for passage of air through the three-dimensional structure, in order to volatize at least one of THC and CBD for inhalation by a user when heat is applied to at least one of the three-dimensional structure or the air passing through the three-dimensional structure.

Embodiment 23 provides the drug delivery product of Embodiment 22 optionally configured such that the three-dimensional structure is a cylindrical shape having multiple layers of the coated substrate, and the three-dimensional structure is formed by rolling the coated substrate into a spiral.

Embodiment 24 provides the drug delivery product of Embodiment 22 optionally configured such that the three-dimensional structure is tubular and includes a longitudinal opening extending from a first end to a second end of the three-dimensional structure, and a cross-section of the three-dimensional structure is a polygon.

Embodiment 25 provides the drug delivery product of Embodiment 22 optionally configured such that the three-dimensional structure is rectangular and includes multiple layers of the coated substrate folded in a saw-tooth pattern and compressed together to form the rectangular shape.

Embodiment 26 provides the drug delivery product of any of Embodiments 22-25 optionally in combination with a drug delivery device configured to receive the three-dimensional structure and comprising a heating element for heating the three-dimensional structure to volatilize the at least one of THC and CBD in the three-dimensional structure into a vapor.

Embodiment 27 provides the drug delivery product of Embodiment 26 optionally configured such that the drug delivery device comprises a mister configured to add a mist to the vapor.

Embodiment 28 provides the drug delivery product of Embodiment 27 optionally configured such that the drug delivery device further comprises a misting reservoir hydraulically connected to the mister.

Embodiment 29 provides the drug delivery product of any of Embodiments 22-28 optionally further comprising one or more additional layers attached to the coated substrate and configured to provide at least one of flavor or enhancement of the at least one of THC and CBD.

Embodiment 30 provides the drug delivery product of any of Embodiments 22-29 optionally configured such that the coated substrate includes first and second electrodes extending laterally on the coated substrate at first and second longitudinal locations, the first and second electrodes each having an electrical resistance sufficient to conduct current laterally such that at least a portion of the coated substrate can be resistively heated, and the at least one of THC and CBD volatilizes into a gas in response to the resistive heating.

Embodiment 31 provides a drug delivery system comprising a coated substrate with one or more coating layers, the one or more coating layers including at least one of THC and CBD, and a heating element for heating the coated substrate to a temperature to volatize the at least one of THC and CBD in the one or more coating layers into a vapor inhalable by a user.

Embodiment 32 provides the drug delivery system of Embodiment 31 optionally configured such that the coated substrate is converted into a drug delivery cartridge configured to maximize surface area of the drug delivery cartridge and allow for passage of air through the drug delivery cartridge, in order to volatize at least one of THC and CBD for inhalation by a user when heat is applied to at least one of the drug delivery cartridge or the air passing through the drug delivery cartridge.

Embodiment 33 provides the drug delivery system of Embodiment 31 or 32 optionally configured such that the heating element is contained within a drug delivery device and the drug delivery cartridge is receivable within a receptacle of the drug delivery device to heat the drug delivery cartridge.

Embodiment 34 provides the drug delivery system of any of Embodiments 31-33 optionally configured such that the heating element is part of a vaporizer or a pipe.

Embodiment 35 provides the drug delivery system of any of Embodiments 31-34 optionally further comprising a mister configured to add a mist to the vapor.

Embodiment 36 provides the drug delivery system of Embodiment 35 optionally further comprising a misting reservoir hydraulically connected to the mister.

Embodiment 37 provides the drug delivery system of any of Embodiments 31-36 optionally configured such that the coated substrate includes first and second electrodes extending laterally on the coated substrate at first and second longitudinal locations, the first and second electrodes each having an electrical resistance sufficient to conduct current laterally along the substrate, the substrate having an electrical resistance high enough to conduct current longitudinally between the first and second electrodes and resistively heat at least a portion of the coated substrate in response to the current conducted therethrough, and the at least one of THC and CBD volatilizes into a gas in response to the resistive heating.

Embodiment 38 provides the drug delivery system of Embodiment 37 optionally configured such that the heating element includes first and second housing electrodes to deliver current between the first and second electrodes on the substrate to resistively heat at least a portion of the coated substrate.

Embodiment 39 provides a drug delivery product including a cylindrical structure extending in a longitudinal direction and formed from a substrate of an electrically conductive material. The cylindrical structure can include first and second electrodes extending laterally on the substrate at respective first and second longitudinal locations, the first and second electrodes each having an electrical resistance sufficient to conduct current laterally along the substrate, and a first substrate portion extending longitudinally between the first and second electrodes, the first substrate portion having an electrical resistance high enough to conduct current longitudinally between the first and second electrodes and resistively heat the first substrate portion in response to the current conducted therethrough. The cylindrical structure can also include a first dose of a drug disposed on the first substrate portion and configured to volatilize into a gas in response to the resistive heating of the first substrate portion.

Embodiment 40 provides the drug delivery product of Embodiment 39 optionally configured such that the substrate is rolled to form the cylindrical structure having a spiral cross-section, when viewed from a longitudinal end of the rolled sheet, and can optionally further comprise a plurality of electrically insulating spacers positioned to space apart adjacent layers of the substrate.

Embodiment 41 provides the drug delivery product of Embodiment 40 optionally configured such that the first and second electrodes are attached to the substrate prior to rolling the substrate to form the cylindrical structure.

Embodiment 42 provides the drug delivery product of any of Embodiments 39-41 optionally further comprising a housing configured to receive the cylindrical structure within a cavity in the housing, the cavity sized and shaped to correspond to the cylindrical structure, the housing having first and second housing electrodes around a circumference of the cavity and facing inward toward the cavity. The first and second housing electrodes can be positioned longitudinally to respectively contact the first and second electrodes of the cylindrical structure when the cylindrical structure is inserted into the housing, and the first and second housing electrodes can be configured to deliver current between the first and second electrodes of the cylindrical structure.

Embodiment 43 provides the drug delivery product of any of Embodiments 39-42 optionally configured such that the cylindrical structure further includes a third electrode extending laterally across the cylindrical structure at a third longitudinal location, so that the second electrode is positioned longitudinally between the first and third electrodes; and the third electrode has an electrical resistance small enough to conduct current laterally along the cylindrical structure. The cylindrical structure further includes a second substrate portion extending longitudinally between the second and third electrodes; and the second substrate portion has an electrical resistance sufficient to conduct current longitudinally between the second and third electrodes and resistively heat the second substrate portion in response to the current conducted therethrough. A second dose of the drug can be disposed on the second substrate portion and configured to volatilize into a gas in response to the resistive heating of the second substrate portion.

Embodiment 44 provides the drug delivery product of Embodiment 43 optionally further comprising a housing configured to receive the cylindrical structure within a cavity in the housing, the cavity sized and shaped to correspond to the cylindrical structure, the housing having first, second, and third housing electrodes around a circumference of the cavity and facing inward toward the cavity, the first, second, and third housing electrodes being positioned longitudinally to respectively contact the first, second, and third electrodes of the cylindrical structure when the cylindrical structure is inserted into the housing, the first and second housing electrodes configured to deliver current between the first and second electrodes of the cylindrical structure, and the second and third housing electrodes configured to deliver current between the second and third electrodes of the cylindrical structure.

Embodiment 45 provides the drug delivery product of Embodiment 44 optionally further comprising a controller positioned in the housing and configured to deliver current between the first and second housing electrodes to provide the first dose of the drug to a patient, and further configured to deliver current between the second and third housing electrodes to provide the second dose of the drug to the patient.

Embodiment 46 provides the drug delivery product of Embodiment 45 optionally configured such that the controller delivers current between the first and second housing electrodes at a first time to provide the first dose of the drug to a user and delivers current between the second and third housing electrodes at a second time, different from the first time, to provide the second dose of the drug to the user.

Embodiment 47 provides the drug delivery product of Embodiment 45 optionally configured such that the controller delivers current between the first and second housing electrodes and simultaneously delivers current between the second and third housing electrodes to provide the first and second doses of the drug to the user at the same time.

Embodiment 48 provides the drug delivery product of any of Embodiments 44-47 optionally configured such that the housing is elongated and includes a first longitudinal end configured to deliver the volatilized gas into a user's mouth.

Embodiment 49 provides the drug delivery product of any of Embodiments 39-48 optionally configured such that the drug includes at least one of tetrahydrocannabinol (THC) or cannabidiol (CBD).

Embodiment 50 provides the drug delivery product of any of Embodiments 39-49 optionally configured such that the first and second electrodes are formed integrally with the substrate and are thicker than the first substrate portion.

Embodiment 51 provides the drug delivery product of any of Embodiments 39-50 optionally configured such that the housing further comprises a mister configured to add a mist to the volatized first dose of the drug.

Embodiment 52 provides the drug delivery product of Embodiment 51 optionally configured such that the housing further comprises a misting reservoir hydraulically connected to the mister.

Embodiment 53 provides an apparatus including a cylindrical structure extending in a longitudinal direction and formed from a substrate of an electrically conductive material. The cylindrical structure can include a plurality of electrodes extending laterally on the substrate at respective longitudinal locations, each electrode in the plurality having an electrical resistance sufficient to conduct current laterally along the substrate. The cylindrical structure can include at least one substrate portion extending longitudinally between the adjacent electrodes in the plurality, each substrate portion having an electrical resistance sufficient to conduct current longitudinally between the adjacent electrodes and resistively heat the substrate portion in response to the current conducted therethrough. The cylindrical structure can include a drug disposed on each substrate portion and configured to volatilize into a gas in response to the resistive heating of the substrate portion Embodiment 54 provides the apparatus of Embodiment 53 optionally configured such that the substrate is rolled to form the cylindrical structure having a spiral cross-section, when viewed from a longitudinal end of the rolled sheet, and optionally further comprising a plurality of electrically insulating spacers positioned to space apart adjacent layers of the substrate.

Embodiment 55 provides the apparatus of Embodiment 54 optionally configured such that the first and second electrodes are attached to the substrate prior to rolling the substrate to form the cylindrical structure.

Embodiment 56 provides the apparatus of any of Embodiments 53-55 optionally configured such that a first lateral end of the substrate is connected to a second lateral end of the substrate to form the cylindrical structure having a tubular shape, and each of the plurality of electrodes extend around an exterior circumference of the tubular shape.

Embodiment 57 provides the apparatus of any of Embodiments 53-56 optionally further comprising a housing configured to receive the cylindrical structure within a cavity sized and shaped to receive the cylindrical structure, the housing having a plurality of housing electrodes around a circumference of the cavity and facing inward toward the cavity, each housing electrode being positioned longitudinally to respectively contact a respective electrode of the cylindrical structure when the cylindrical structure is inserted into the housing. Each pair of adjacent housing electrodes can be configured to deliver current between a corresponding pair of adjacent electrodes of the cylindrical structure.

Embodiment 58 provides the apparatus of Embodiment 57 optionally further comprising a controller positioned in the housing and configured to deliver current between adjacent pairs of housing electrodes at sequential times to provide a dose of the drug to a user at each sequential time, or deliver current between adjacent pairs of housing electrodes simultaneously to provide more than one dose of the drug to the user at one time.

Embodiment 59 provides the apparatus of any of Embodiments 53-58 optionally configured such that the drug includes at least one of THC or CBD.

Embodiment 60 provides the apparatus of any of Embodiments 53-59 optionally configured such that the housing further comprises a mister configured to add a mist to the volatilized drug.

Embodiment 61 provides the apparatus of Embodiment 60 optionally configured such that the housing further comprises a misting reservoir hydraulically connected to the mister.

Embodiment 62 provides a method including forming or providing a sheet of conductive material, the sheet extending in longitudinal and lateral dimensions, the sheet having a plurality of contact portions spaced apart longitudinally and extending laterally across the sheet, the sheet having at least one substrate portion extending longitudinally between a pair of adjacent contact portions, the contact portions having a thickness greater than a thickness of the at least one substrate portion. The method including depositing a drug on the at least one substrate portion, the drug configured to volatilize into a gas in response to resistive heating of the respective substrate portion, and converting the sheet into a cylindrical structure.

Embodiment 63 provides the method of Embodiment 62 optionally configured such that converting the sheet into a cylindrical structure includes rolling the sheet such that the cylindrical structure has a spiral cross-section, when viewed from a longitudinal end of the rolled sheet. The method can optionally further comprise, as the sheet is rolled, placing a plurality of electrically insulating spacers between adjacent layers of the sheet, the spacers being spaced apart to allow a flow of gas therearound.

Embodiment 64 provides the method of Embodiment 62 or 63 optionally configured such that converting the sheet into a cylindrical structure includes connecting a first lateral end of the sheet to a second lateral end of the sheet to form the cylindrical structure having a tubular shape, and each of the plurality of contact portions extends around a circumference of the tubular shape.

Embodiment 65 provides the method of any of Embodiments 62-64 optionally configured such that the cylindrical structure is configured for use as a drug delivery cartridge.

Embodiment 66 provides the method of any of Embodiments 62-65 wherein the drug includes at least one of THC or CBD.

Embodiment 67 provides a method, system, product or apparatus of any one or any combination of Embodiments 1-66, which can be optionally configured such that all steps or elements recited are available to use or select from.

What is claimed is:

1. A drug delivery product, comprising:
a cylindrical structure extending in a longitudinal direction and formed from a substrate of an electrically conductive material, the cylindrical structure comprising:
first and second electrodes extending laterally on the substrate at respective first and second longitudinal locations, the first and second electrodes each having an electrical resistance sufficient to conduct current laterally along the substrate;
a first substrate portion extending longitudinally between the first and second electrodes, the first substrate portion having an electrical resistance high enough to conduct current longitudinally between the first and second electrodes and resistively heat the first substrate portion in response to the current conducted therethrough;
a plurality of electrically insulating spacers positioned to space apart adjacent layers of the substrate; and
a first dose of a drug disposed on the first substrate portion and configured to volatilize into a gas in response to the resistive heating of the first substrate portion,
wherein the substrate is rolled to form the cylindrical structure having a spiral cross-section, when viewed from a longitudinal end of the rolled substrate.

2. The drug delivery product of claim 1, wherein the first and second electrodes are attached to the substrate prior to rolling the substrate to form the cylindrical structure.

3. The drug delivery product of claim 1, further comprising:
a housing configured to receive the cylindrical structure within a cavity in the housing, the cavity sized and shaped to correspond to the cylindrical structure,
the housing having first and second housing electrodes around a circumference of the cavity and facing inward toward the cavity,
the first and second housing electrodes being positioned longitudinally to respectively contact the first and second electrodes of the cylindrical structure when the cylindrical structure is inserted into the housing,
the first and second housing electrodes configured to deliver current between the first and second electrodes of the cylindrical structure.

4. The drug delivery product of claim 1,
wherein the cylindrical structure further includes a third electrode extending laterally across the cylindrical structure at a third longitudinal location, so that the second electrode is positioned longitudinally between the first and third electrodes;
wherein the third electrode has an electrical resistance small enough to conduct current laterally along the cylindrical structure,
wherein the cylindrical structure further includes a second substrate portion extending longitudinally between the second and third electrodes;
wherein the second substrate portion has an electrical resistance sufficient to conduct current longitudinally between the second and third electrodes and resistively heat the second substrate portion in response to the current conducted therethrough; and
wherein a second dose of the drug is disposed on the second substrate portion and configured to volatilize into a gas in response to the resistive heating of the second substrate portion.

5. The drug delivery product of claim 4, further comprising:
a housing configured to receive the cylindrical structure within a cavity in the housing, the cavity sized and shaped to correspond to the cylindrical structure,
the housing having first, second, and third housing electrodes around a circumference of the cavity and facing inward toward the cavity,
the first, second, and third housing electrodes being positioned longitudinally to respectively contact the first, second, and third electrodes of the cylindrical structure when the cylindrical structure is inserted into the housing,
the first and second housing electrodes configured to deliver current between the first and second electrodes of the cylindrical structure,
the second and third housing electrodes configured to deliver current between the second and third electrodes of the cylindrical structure.

6. The drug delivery product of claim 5, further comprising:
a controller positioned in the housing and configured to deliver current between the first and second housing electrodes to provide the first dose of the drug to a patient, and further configured to deliver current between the second and third housing electrodes to provide the second dose of the drug to the patient.

7. The drug delivery product of claim 6, wherein the controller delivers current between the first and second housing electrodes at a first time to provide the first dose of the drug to a user and delivers current between the second and third housing electrodes at a second time, different from the first time, to provide the second dose of the drug to the user.

8. The drug delivery product of claim 5, wherein the housing further comprises a mister configured to add a mist to the volatized first dose of the drug.

9. The drug delivery product of claim 8, wherein the housing further comprises a misting reservoir hydraulically connected to the mister.

10. The drug delivery product of claim 1, wherein the first and second electrodes are formed integrally with the substrate and are thicker than the first substrate portion.

11. A drug delivery product, comprising:
a cylindrical structure extending in a longitudinal direction and formed from a substrate of an electrically conductive material, the cylindrical structure comprising:
first and second electrodes extending laterally on the substrate at respective first and second longitudinal locations, the first and second electrodes each having an electrical resistance sufficient to conduct current laterally along the substrate;
a first substrate portion extending longitudinally between the first and second electrodes, the first substrate portion having an electrical resistance high enough to conduct current longitudinally between the first and second electrodes and resistively heat the first substrate portion in response to the current conducted therethrough;
a first dose of a drug disposed on the first substrate portion and configured to volatilize into a gas in response to the resistive heating of the first substrate portion;
a third electrode extending laterally across the cylindrical structure at a third longitudinal location, so that the second electrode is positioned longitudinally between the first and third electrodes, the third electrode having an electrical resistance small enough to conduct current laterally along the cylindrical structure;
a second substrate portion extending longitudinally between the second and third electrodes, the second substrate portion having an electrical resistance sufficient to conduct current longitudinally between the second and third electrodes and resistively heat the second substrate portion in response to the current conducted therethrough;
a second dose of the drug is disposed on the second substrate portion and configured to volatilize into a gas in response to the resistive heating of the second substrate portion; and
a housing configured to receive the cylindrical structure within a cavity in the housing, the cavity sized and shaped to correspond to the cylindrical structure,
the housing having first, second, and third housing electrodes around a circumference of the cavity and facing inward toward the cavity,
the first, second, and third housing electrodes being positioned longitudinally to respectively contact the first, second, and third electrodes of the cylindrical structure when the cylindrical structure is inserted into the housing,
the first and second housing electrodes configured to deliver current between the first and second electrodes of the cylindrical structure,
the second and third housing electrodes configured to deliver current between the second and third electrodes of the cylindrical structure.

12. The drug delivery product of claim 11, further comprising:
a controller positioned in the housing and configured to deliver current between the first and second housing electrodes to provide the first dose of the drug to a patient, and further configured to deliver current between the second and third housing electrodes to provide the second dose of the drug to the patient.

13. The drug delivery product of claim 12, wherein the controller delivers current between the first and second housing electrodes at a first time to provide the first dose of the drug to a user and delivers current between the second and third housing electrodes at a second time, different from the first time, to provide the second dose of the drug to the user.

14. The drug delivery product of claim 11, wherein the first and second electrodes are formed integrally with the substrate and are thicker than the first substrate portion.

15. The drug delivery product of claim 11, wherein the housing further comprises a mister configured to add a mist to the volatized first dose of the drug.

16. The drug delivery product of claim 15, wherein the housing further comprises a misting reservoir hydraulically connected to the mister.

* * * * *